US009267918B2

(12) United States Patent
Joaquim et al.

(10) Patent No.: US 9,267,918 B2
(45) Date of Patent: Feb. 23, 2016

(54) MICROFLUIDIC SYSTEMS

(71) Applicants: Tony R. Joaquim, Mount Laurel, NJ (US); Lewis Joe Stafford, Newark, DE (US); Ross Stewart Chambers, Hockessin, DE (US); Xin Liu, Cambridge (GB); Clive Adrian Smith, Hertford (GB); Xin Li, Cambridge (GB); Graeme Whyte, Cambridge (GB)

(72) Inventors: Tony R. Joaquim, Mount Laurel, NJ (US); Lewis Joe Stafford, Newark, DE (US); Ross Stewart Chambers, Hockessin, DE (US); Xin Liu, Cambridge (GB); Clive Adrian Smith, Hertford (GB); Xin Li, Cambridge (GB); Graeme Whyte, Cambridge (GB)

(73) Assignees: Cambridge Enterprise Limited, Cambridgeshire (GB); Sphere Fluidics Limited, Cambridge (GB); SDIX, LLC, Rockville, MD (US)

( * ) Notice: Subject to any disclaimer, the term of this patent is extended or adjusted under 35 U.S.C. 154(b) by 479 days.

(21) Appl. No.: 13/725,459

(22) Filed: Dec. 21, 2012

(65) Prior Publication Data
US 2014/0021049 A1 Jan. 23, 2014

Related U.S. Application Data

(63) Continuation-in-part of application No. 12/738,268, filed as application No. PCT/GB2008/050944 on Oct. 16, 2008, now Pat. No. 8,828,210.

(30) Foreign Application Priority Data

Oct. 16, 2007 (GB) .................................. 0720202.1

(51) Int. Cl.
*G01N 27/447* (2006.01)
*G01N 15/14* (2006.01)
(Continued)

(52) U.S. Cl.
CPC .... *G01N 27/44791* (2013.01); *B01L 3/502784* (2013.01); *G01N 15/1484* (2013.01); *B01L 3/0268* (2013.01); *B01L 2200/0652* (2013.01); *B01L 2200/0673* (2013.01);
(Continued)

(58) Field of Classification Search
CPC .................................. B01L 3/5027–3/502792
See application file for complete search history.

(56) References Cited

U.S. PATENT DOCUMENTS 3,710,933 A 1/1973 Fulwyler et al.
5,292,416 A * 3/1994 Novotny et al. ............... 204/453
(Continued)

FOREIGN PATENT DOCUMENTS

DE 102010 12 580 A1 9/2011
EP 1 334 347 3/2002
(Continued)

OTHER PUBLICATIONS

Ahn et al., "Dielectrophoretic Manipulation of Drops for High-Speed Microfluidic Sorting Devices," Applied Physics Letters, 88:024104 (3 pages) (2006).
(Continued)

*Primary Examiner* — J. Christopher Ball
(74) *Attorney, Agent, or Firm* — Foley & Lardner LLP

(57) ABSTRACT

A flow cell for a microfluidic device can include a chamber, first microfluidic entry and exit channels, second microfluidic entry and exit channels, a first electrode, and a second electrode. A microfluidic device can include a microfluidic channel, a laser to excite fluorescent material, and a detector to detect fluorescence emission. Methods of merging a droplet from an emulsion in to a second stream of fluid and of detecting a content of a droplet in a stream are further disclosed.

18 Claims, 19 Drawing Sheets

(51) Int. Cl.
*B01L 3/00* (2006.01)
*B01L 3/02* (2006.01)

(52) U.S. Cl.
CPC ... *B01L 2400/043* (2013.01); *B01L 2400/0415* (2013.01); *G01N 2015/149* (2013.01)

(56) References Cited

U.S. PATENT DOCUMENTS

| | | | |
|---|---|---|---|
| 6,140,048 | A | 10/2000 | Muller et al. |
| 2001/0048637 | A1 | 12/2001 | Weigl et al. |
| 2004/0005628 | A1 | 1/2004 | Foster |
| 2004/0115838 | A1 | 6/2004 | Quake et al. |
| 2004/0211659 | A1 | 10/2004 | Velev |
| 2004/0219078 | A1 | 11/2004 | Kitamori et al. |
| 2004/0233424 | A1 | 11/2004 | Lee et al. |
| 2005/0128479 | A1 | 6/2005 | Gilbert et al. |
| 2006/0280029 | A1 | 12/2006 | Garstecki et al. |
| 2012/0091004 | A1 | 4/2012 | Abell et al. |

FOREIGN PATENT DOCUMENTS

| | | |
|---|---|---|
| EP | 1 380 337 A2 | 4/2004 |
| EP | 1 658 133 | 3/2005 |
| EP | 2 139 984 | 10/2008 |
| EP | 2 047 910 B1 | 1/2012 |
| WO | WO-96/12541 A1 | 5/1996 |
| WO | WO-99/64840 A1 | 12/1999 |
| WO | WO-02/23163 A1 | 3/2002 |
| WO | WO-2004/071638 A2 | 8/2004 |
| WO | WO-2005/021151 A1 | 3/2005 |
| WO | WO-2007/081387 A1 | 7/2007 |
| WO | WO-2008/130871 A2 | 10/2008 |
| WO | WO-2011/005776 A1 | 1/2011 |
| WO | WO-2011/129956 A1 | 10/2011 |

OTHER PUBLICATIONS

Ahn et al., "Electrocoalescence of Drops Synchronized by Size-Dependent Flow in Microfluidic Channels," Applied Physics Letters 88:264105 (3 pages) (2006).
Anna et al., "Formation of Dispersions Using 'Flow Focusing' in Microchannels," Applied Physics Letters, 82:364 (2003).
Bibette et al., "Emulsions: Basic Principles," Reports on Progress in Physics—IOP Science, 62:969-1033 (1999).
Search Report for corresponding United Kingdom Application No. GB0720202.1, dated Feb. 15, 2008.
Horiba, "Fluorolog-3, How to Build a Spectrofluorometer," Horiba Jobin Yvon (2005).
International Preliminary Report on Patentability for corresponding Application No. PCT/GB2008/050944, dated Apr. 20, 2010.
International Search Report for corresponding Application No. PCT/GB2008/050944 dated Dec. 28, 2009.
Kralj et al., "Surfactant-Enhanced Liquid-Liquid Extraction in Microfluidic Channels With Inline Electric-Field Enhanced Coalescence," Lab Chip, 5:531-535 (2005).
Siegel et al., "Microsolidics: Fabrication of Three-Dimensional Metallic Microstructures in Poly(dimethylsiloxane)," Advanced Materials, 19:727-733 (2007).
Wehry, "Molecular Fluorescence and Phosphorescence Spectrometry," Handbook of Instrumental Techniques for Analytical Chemistry, 507-539 (1997).
Notice of Allowance received in U.S. Appl. No. 12/738,268 dated Apr. 29, 2014.

* cited by examiner

MICROFLUIDIC SYSTEMS

PRESENT APPLICATION

The present application is a continuation-in-part of pending application U.S. Ser. No. 12/738,268 published as US2012/0091004 A1, derived from PCT/GB08/050,944 and claiming priority from GB0720202.1.

FIELD OF THE INVENTION

This invention relates to microfluidic systems and more particularly to flow cells, a microfluidic device, a method of merging a droplet from an emulsion into a second stream of fluid, and a method of detecting a content of a droplet in a stream of fluid.

BACKGROUND TO THE INVENTION

Micro droplets show great promise as a new high-throughput technology in chemistry, biochemistry and molecular biology. Micro droplets can be generated at rates in excess of several thousand per second and accurately formulated using minute amounts of small molecules, DNA, proteins or cells. Furthermore, integrated active elements can be used to control individual droplets. With technology for creating, dividing, fusing, interrogating and even sorting micro droplets already developed, one of the main problems to be resolved is how to access their contents.

Droplets are naturally self-contained microreactors that prevent sample loss, diffusion and cross-contamination, general issues that afflict traditional microfluidics. However, the isolated nature of droplets prevents physical access of their contents on-chip. Even though this does not represent a problem for many of the applications that have already been demonstrated, it limits the integration of microdroplets with other platforms. Analytical techniques such as mass spectrometry, capillary electrophoresis or liquid chromatography have been successfully integrated with continuous flow microfluidic devices, but their integration with microdroplets remains hindered.

Background prior art relating to microdroplets can be found in: K. Ahn, J. Agresti, H. Chong, M. Marquez, D. A. Weitz, *Applied Physics Letters* 2006, 88, 264105; L. M. Fidalgo, C. Abell, W. T. S. Huck, *Lab Chip* 2007, 7, 948; Y.-C. Tan, J. S. Fisher, A. I. Lee, V. Cristini, A. P. Lee, *Lab Chip* 2004, 4, 292; P. S. Dittrich, M. Jahnz, P. Schwille, *ChemBioChem* 2005, 6, 811; K. Ahn, C. Kerbage, T. P. Hunt, R. M. Westervelt, D. R. Link, D. A. Weitz, *Appl. Phys. Lett.* 2006, 88, 024104; P. S. Dittrich, K. Tachikawa, A. Manz, *Anal. Chem.* 2006, 78, 3887; J. Bibette, F. L. Calderon, P. Poulin, *Rep. Prog. Phys.* 1999, 62, 969; J. S. Eow, M. Ghadiri, A. O. Sharif, T. J. Williams, *Chemical Engineering Journal* 2001, 84, 173; P. Atten, *Journal of Electrostatics* 1993, 30, 259; J. G. Kralj, M. A. Schmidt, K. F. Jensen, *Lab Chip* 2005, 5, 531; C. Priest, S. Herminghaus, R. Seemann, *Appl. Phys. Lett.* 2006, 89, 134101; "Phase separation of segmented flow by the photocatalytic wettability patterning and tuning of microchannel surface", Go Takei, Arata Aota, Akihide Hibara, Takehiko Kitamori and Haeng-Boo Kim, Eleventh International Conference on Miniaturized systems for Chemistry and Life Sciences, 7-11 Oct. 2007, Paris, France; and also WO2005/021151, WO2007/081387, US2001/0048637, US2004/0219078, EP1380337, and US2006/0280029.

Further background art is provided by: EP1334347A1; US2004/0233424 A1; EP1658133 A1; EP2047910 B; EP2139984 A1; and WO2011005776 A1, and further by: U.S. Pat. No. 6,140,048 A; DE102010012580 A; US2004115838 A; US2005128479A; U.S. Pat. No. 3,710,933A; WO9964840A; US201129422A; US2004005628A; WO2004/071638 A2; WO96/12541; and US2004/0211659 A1, and non-patent literature "Molecular Fluorescence and Phosphorescence Spectrometry" (Earl L. Wehry, University of Tennessee) and "Fluorolog-3," How to Build a Spectrofluorometer (Jobin Yvon Horiba).

There therefore remains a need for improved techniques for accessing the contents of microdroplets.

SUMMARY OF THE INVENTION

In a first aspect of the invention, there is provided a flow cell for a microfluidic device for accessing the contents of a droplet of an emulsion in a microfluidic system, the flow cell having: a chamber; a first microfluidic entry channel and first microfluidic exit channel for flowing said emulsion through said chamber, and a second microfluidic entry channel and second microfluidic exit channel for flowing a stream of second fluid through said chamber, wherein said first microfluidic entry and exit channels and a wall of said chamber are substantially aligned whereby flow of said emulsion through the flow cell is substantially straight, wherein an angle between a longitudinal axis of said first microfluidic entry channels at said chamber and a longitudinal axis of said second microfluidic entry channel at said chamber is acute, and an angle between a longitudinal axis of said first microfluidic exit channel at said chamber and a longitudinal axis of said second microfluidic exit channel at said chamber is acute, wherein, in operation, an interface is formed in said chamber between said emulsion and said stream of second fluid, and said acute angle between said entry channels causes tangential approach of the flow of said second fluid to the flow of said emulsion, whereby, in operation, said droplet coalesces with said stream of second fluid and said contents of said droplet in said second stream are accessible from said second stream of fluid from said second microfluidic exit channel.

A schematic showing a shape of a flow cell embodiment is shown in FIG. 5b, and an implementation of a flow cell embodiment is shown in FIG. 6. In a preferred embodiment, a substantially ('substantially' including at least exactly) k-shaped flow cell may provide a tangential approach of one flow to another substantially straight flow, this in embodiments helping droplets to merge into a second fluid. (Noting that any fluid or stream mentioned throughout this document may comprise one or more components, e.g., surfactant(s)). The longitudinal axis of each channel at the chamber is generally perpendicular to a radial axis if the channel is circular in cross-section, and/or is generally the same as the direction of flow in the channel as the emulsion is about to enter the chamber or has just exited the chamber (as appropriate).

There may further be provided the flow cell, wherein at least one of width of the first microfluidic entry channel at the chamber and width of the first microfluidic exit channel at the chamber is within about 20 micrometers to about 500 micrometers, preferably about 50 micrometers to about 300 micrometers, more preferably about 100 micrometers to about 250 micrometers.

There may further be provided the flow cell, wherein at least one of width of the second microfluidic entry channel and width of the second microfluidic exit channel is within about 10 micrometers to about 500 micrometers, preferably about 20 micrometers to about 300 micrometers, more preferably about 50 micrometers to about 200 micrometers.

There may further be provided the flow cell, wherein a distance between said first microfluidic entry channel and said second microfluidic entry channel at the chamber, and/or between said first microfluidic exit channel and said second microfluidic exit channel at the chamber, is within the range of about 0 micrometers to about 500 micrometers, preferably about 5 micrometers to about 300 micrometers, more preferably about 10 micrometers to about 250 micrometers. Thus, there may be a gap between the first and second entry channels at the chamber and/or between the first and second exit channels at the chamber, each such gap adding to the width of the chamber.

There may further be provided the flow cell having a length within a range of about 10 micrometers to about 2000 micrometers, preferably about 50 micrometers to about 1000 micrometers, more preferably about 100 micrometers to about 500 micrometers.

There may further be provided the flow cell, wherein the first and second microfluidic entry and exit channels and chamber have depths within a range of about 5 micrometers to about 500 micrometers, preferably about 10 micrometers to about 300 micrometers, more preferably about 20 micrometers to about 150 micrometers.

Generally, an acute angle corresponds to greater than zero and less than ninety degrees. However, there may further be provided the flow cell, wherein the acute angle between the first and second microfluidic entry channels is within a range of about 30 to 90 degrees, more preferably about 60 to about 90 degrees. There may further be provided the flow cell, wherein the acute angle between the first and second microfluidic entry channels is within a range of about 20 to about 70 degrees, more preferably about 40 to about 60 degrees. An angle between the longitudinal axes of the entry channels at the chamber, and/or an angle between the longitudinal axes of the exit channels at the chamber, is/are preferably greater than 90 degrees (similarly as for the angle between channels having axes a and c in FIG. 17).

In another aspect of the invention, there is provided a flow cell for a microfluidic device for accessing the contents of a droplet of an emulsion in a microfluidic system, the flow cell having: a chamber; a first microfluidic entry channel and first microfluidic exit channel for flowing said emulsion through said chamber; a second microfluidic entry channel and second microfluidic exit channel for flowing a stream of second fluid through said chamber; a first electrode having an edge facing a first side of the chamber between the first microfluidic entry channel and the first microfluidic exit channel, said edge substantially straight and substantially parallel to said first side of the chamber; and a second electrode having an edge facing a second side of the chamber between the second microfluidic entry channel and the second microfluidic exit channel, said edge substantially straight and substantially parallel to said second side of the chamber, wherein, in operation, an interface is formed in said chamber between said emulsion and said stream of second fluid, wherein, in operation, said droplet coalesces with said stream of second fluid and said contents of said droplet in said second stream are accessible from said second stream of fluid from said second microfluidic exit channel.

An embodiment having electrode(s) with, e.g., a substantially flat edge along the droplet flow direction, e.g., pointed electrodes, may allow a droplet to become more distorted and/or become and remain distorted as it travels along a relatively long path. The length of such a path may substantially correspond to the length of the edge(s) and/or the extent of the field between the electrodes, the field lines preferably substantially perpendicular to the droplet flow path and/or the field optionally having substantially uniform field strength along the flow path. Such an embodiment may allow more reliable controlled coalescence and/or droplet selection.

There may further be provided the flow cell, wherein at least one said edge has length within a range of about 10 micrometers to about 2000 micrometers, preferably about 50 micrometers to about 1000) micrometers, more preferably about 100 micrometers to about 500 micrometers.

There may further be provided the flow cell, wherein at least one of said edges is separated from the chamber by a distance within a range of about 1 micrometer to about 200 micrometers, preferably about 10 micrometers to about 150 micrometers, more preferably about 20 micrometers to about 100 micrometers.

There may further be provided the flow cell, wherein a thickness of at least one of said electrodes is within a range of about 1 nanometer to about 500 millimeters, preferably about 100 nanometers to about 500 micrometers, more preferably about 200 nanometers to about 150 micrometers.

An alternative flow cell arrangement is as defined above but has the first and second electrodes each having a substantially pointed edge (rather than the substantially straight and substantially parallel edges). The point(s) of each electrode is/are generally directed towards the chamber. The internal angle of each such point is preferably without 0 to about 180 degrees, more preferably between about 20 and about 120 degrees, yet more preferably between about 50 and about 90 degrees. Such an arrangement, or the above flow cell having the substantially straight and substantially parallel edges, may be found in an embodiment wherein the flow cell of the first aspect, e.g., a K-shaped flow cell.

In another aspect of the invention, there is provided a microfluidic device for detecting a content of a droplet in a stream of fluid, the device comprising; a microfluidic channel arranged to conduct said stream of fluid; a laser configured to output a laser beam having a wavelength to excite a fluorescent material to output a fluorescence emission; and a detector having an optical fibre comprising an end facing the microfluidic channel, said end configured to receive said fluorescence emission, the detector arranged to detect a said fluorescence emission propagated through the optical fibre, wherein a position of excitation of said fluorescence emission in said microfluidic channel is offset from a part of said microfluidic channel facing the end of the optical fibre.

An embodiment of this aspect may provide for fluorescence detection using an optical fibre setup, including a 90 degree set-up (see FIGS. 8b and 9) between the excitation laser beam and optical fibre, and offset (see FIG. 9) between excitation and emission detection points for application to, e.g., time resolved FRET assay.

There may further be provided the microfluidic device, configured such that duration of flow of said droplet from position of excitation to said part of said microfluidic channel facing the end of the optical fibre is within a range of about 1 nanosecond to about 1 millisecond, preferably about 1 microsecond to about 500 microseconds, more preferably about 10 microseconds to about 500 microseconds.

There may further be provided the microfluidic device, wherein said end of said optical fibre is separated from the microfluidic channel by a distance of less than about 200 micrometers, preferably between about 5 to about 100 micrometers, more preferably about 10 to about 50 micrometers.

There may further be provided the microfluidic device, wherein the optical fibre has an optical axis substantially perpendicular to the microfluidic channel.

There may further be provided the microfluidic device, wherein the laser is arranged to provide said laser beam at substantially 90 degrees to said optical fibre.

There may further be provided the microfluidic device, comprising a first electrode facing a first side of the chamber and a second electrode facing an second side of the chamber, said second side opposing said first side, the device configured to apply an electric field pulse between said electrodes at a fixed delay after a said fluorescence emission is detected by said detector, if said fluorescence emission exceeds an emission intensity threshold.

There may further be provided the microfluidic device, wherein said delay is within a range of about 1 microsecond to about 1 second, preferably about 500 microseconds to about 500 milliseconds, more preferably about 1 millisecond to about 100 milliseconds.

There may further be provided the microfluidic device of claim 18, configured to apply across said electrodes a voltage to generate said electric field pulse, said voltage within a range of about 10 voltage to about 2000 volts, preferably about 100 volts to about 1000 volts, more preferably about 400 volts to about 800 volts.

In another aspect of the invention, there is provided a method of merging a droplet from an emulsion into a second stream of fluid, the method comprising applying an electric or magnetic field across a flow of said emulsion, the method further comprising controlling a shape of an edge of said field waveform to distort a shape of the droplet such that said droplet when distorted touches said second stream of fluid, the droplet thereby merging with the second stream.

In an embodiment, distortion of droplet at the time of either or both edges of such a waveform, e.g., pulse preferably rectangular, increases probability of droplet merging into a second stream of fluid. This may in practice done by adjusting the timing and/or magnitude of pulse edge(s).

There may further be provided the method, wherein said controlling said waveform edge shape comprises changing a slew rate of said edge.

There may further be provided the method, wherein said waveform having said controlled edge shape is a triangular or ramp waveform.

There may further be provided the method, wherein said controlled edge shape is curved, preferably such that a shape of the waveform is substantially sinusoidal.

There may further be provided the method of claim 22, wherein said controlled edge shape is comprises a plurality of pulses, preferably each pulse starting from a substantially same value.

A related a method of merging a droplet from an emulsion into a second stream of fluid comprises applying a series of an electric or magnetic field pulses across a flow of said emulsion, said series controlling a distorting of a shape of the droplet such that said droplet touches said second stream of fluid, the droplet thereby merging with the second stream.

In another aspect of the invention, there is provided a method of detecting a content of a droplet in a stream of fluid, the method comprising exciting and detecting fluorescence emission of a content of the droplet, wherein said content comprises a fluorescent material comprising a fluorescent labelled antibody for binding to a cell surface marker, protein, peptide, carbonate or DNA dissolved in said content of said droplet and cellular probes which detect cell function and viability.

In another aspect of the invention, there is provided a method of detecting a content of a droplet in a stream of aqueous fluid carrying at least one said droplet, said at least one said droplet having on average one biological cell per droplet, the method comprising: storing a said biological cell in said droplet for substantially 30 minutes or more, wherein said droplet is in said aqueous fluid and said aqueous fluid is a culture medium. Any above-described flow cell, microfluidic device and/or method may be used to detect a result of biological activity in said stored cell or a biological molecule or chemical released or secreted from said stored cell. In an example, droplets containing more than one cell, say ten cells per droplet, are screened, for example when looking for a rare clone as a first round of screening prior to a second round of screening at fewer cells, e.g. one cell, per droplet. In another example looks for a biological interaction of one or more different cell types upon another cell type; such influence could be to promote cell growth or protein expression or to cause cell death.

In another aspect, there is provided a flow cell for a microfluidic device for accessing the contents of a droplet of an emulsion in a microfluidic system, the flow cell having: a chamber; a first microfluidic entry channel and first microfluidic exit channel for flowing said emulsion through said chamber; and a second microfluidic entry channel and second microfluidic exit channel for flowing a stream of second fluid through said chamber, wherein an angle between a longitudinal axis of said first microfluidic entry channels at said chamber and a longitudinal axis of said second microfluidic entry channel at said chamber is acute, and an angle between a longitudinal axis of said first microfluidic exit channel at said chamber and a longitudinal axis of said second microfluidic exit channel at said chamber is acute, wherein, in operation, an interface is formed in said chamber between said emulsion and said stream of second fluid, and said acute angle between said entry channels causes tangential approach of the flow of said second fluid to the flow of said emulsion, whereby, in operation, said droplet coalesces with said stream of second fluid and said contents of said droplet in said second stream are accessible from said second stream of fluid from said second microfluidic exit channel.

The flow cell may have an angle between the first microfluidic entry channel and the length direction of the flow cell or chamber within the range between 0 and about 90 degrees, preferably between 0 and about 45 degrees, and further preferably between 0 and about 10 degrees. Additionally or alternatively, the flow cell may have an angle between the first microfluidic exit channel and the length direction of the flow cell or chamber within the range between 0 and about 90 degrees, preferably between 0 and about 45 degrees, and further preferably between 0 and about 10 degrees. Such a length direction of the flow cell or chamber may be e.g., a direction of a longitudinal axis of the (preferably substantially square, rectangular or at least partially cylindrical) chamber, or direction of flow through the chamber at least at the centre of the chamber, or direction of a wall of said chamber most closely aligned to such a flow direction.

Part of such a flow cell is shown in FIG. 17, which shows a chamber and the entry (or exit) channels with acute angles between axes a and b and between b and c. The two angles are considered together. i.e. angle between lines a and c, is preferably more than 90 degrees.

In any of the above aspects, without or without any of the above optional features, the time delay between successive droplets passing through the flow cell or microfluidic channel, e.g., past an emission, detection and/or selection position, may be, for example, greater than or equal to: about 0.01 ms, about 0.1 ms, about 1 ms or about 10 ms.

Moreover, any reference to 'micro' within this specification may encompass "pico", e.g., a microdroplet referred to in regard to any embodiment described herein may be a picodroplet.

Any two or more of the above-described aspects and/or optional features of embodiments of the invention may be combined in any permutation, advantageously for time resolved fluorescence assays or luminescence oxygen channeling assays.

The following methods, devices and systems may be provided in any combination or permutation of any one or more of above aspects (preferably with any one or more of the optional features of the aspects as set out above).

A first method of accessing the contents of a droplet of an emulsion in a microfluidic system comprises: flowing the emulsion alongside a continuous, non-emulsive stream of second fluid to provide an interface between said emulsion and said stream of second fluid; and applying one or both of an electric and magnetic field across said interface to alter a trajectory of a said droplet of said emulsion to cause said droplet to coalesce with said stream of second fluid; and accessing said contents of said droplet in said second stream.

The method may enable the contents of microdroplets to be readily extracted on demand, discarding the carrier fluid, and converting them into a continuous stream. This in turn enables microfluidic functionality to be combined with the advantages provided by microdroplets.

The emulsion in the method may comprise a dispersed phase of water in oil and the second fluid comprises an aqueous fluid; potentially double emulsions may be employed. The applied field may comprise an electric field, a magnetic field, or a combination of the two which includes, for example, laser light (not limited to visible wavelength). This de-stabilises the interface between the emulsion and the second fluid and thus enables the drop to coalesce with the second fluid, thus enabling the contents of the droplet to be analysed or otherwise further processed using microfluidic techniques. Some implementations of the method are so effective that there is substantially no oil in the continuous stream of second fluid and the contents of the droplet are as if they had never been in the emulsion in the first place. As the skilled person would understand the presence of oil in the output stream would make many microfluidic analytical techniques impractical or impossible.

In some preferred implementations of the method one or more properties of the droplets are detected and the electric and/or magnetic fields are applied to selectively merge the droplet with the second stream. For example a fluorescence of the droplet may be detected to determine the presence or absence of a substance within the droplet. To facilitate selection the field may be pulsed and the duration of a pulse adjusted so that only a single droplet is present, for example between a pair of electrodes or in a laser beam, during a pulse. The pulse may comprise a pulse above or below a base line level of the field.

The applied field may comprise an electric field applied with a pair of electrodes and disposed laterally either side of the stream of emulsion and the stream of second (aqueous) fluid. The electric field may be substantially perpendicular to laminar flows of the two streams. A droplet may flow past the interface between the two streams at a distance of greater than 1 micrometer from the interface. Preferably therefore the electric field has a value at the interface of at least $10^6$ volts per meter, preferably of the order of $10^7$ volts per meter.

There is a particular need for high-throughput systems, that is systems capable of processing droplets at rates faster than 1 KHz, 5 KHz or, preferably, 10 KHz droplets per second.

This is useful, for example, when screening a large library of items. At high throughputs the above-described techniques can be difficult to apply because droplets are closely spaced in the stream of emulsion. However, the above described techniques need not rely upon the application of an electric and/or magnetic field to cause the droplet to coalesce with the second stream of fluid; instead this may be performed using the geometry of the microfluidic system, but configuring the geometry so as to cause a droplet to collide with the interface between the emulsion and the stream of second fluid. Again this effectively de-stabilises this interface.

A second method of accessing the contents of a droplet of an emulsion in a microfluidic system comprises: flowing the emulsion alongside a continuous, non-emulsive stream of second fluid such that said droplet coalesces with said stream of second fluid; and accessing said contents of said droplet in said second stream.

The geometry of microfluidic channels carrying the stream of emulsion and the stream of second fluid may be arranged so that there is a region, for example a chamber, in which a droplet collides with the interface between these two streams, enabling the droplet to coalesce with the second stream. One way in which this may be achieved is by confining a droplet within a microfluidic channel so that the channel constrains the droplet into a shape different to that which, unconstrained, surface forces would cause it to adopt. This confined droplet is then allowed to expand into a chamber in which the interface is located so that a surface of the droplet is brought into contact with the interface, hence de-stabilising the interface and causing the droplet to coalesce with the second stream of fluid (here "expand" will be understood to be referring to expansion in one or more dimensions in which the droplet is constrained within the microfluidic channel, since the droplet volume per se remains unchanged).

Preferably the method is implemented in a four-port chamber, with inlet and outlet ports for the stream of emulsion and inlet and outlet ports for the stream of second fluid.

A technique such as that described above enables screening to take place in two stages, a first stage in which a droplet is selectively directed into one of two or more microfluidic channels, for example responsive to a detected signal such as fluorescence. downstream one (or more) of these channels is then directed to a region in which droplets of an emulsion stream in that channel coalesce with the stream of second fluid. The contents of the droplets selected upstream may be accessed via the stream of second fluid, for example for analysis by any of a range of microfluidic techniques such as will be well known to those skilled in the art.

A third method of microfluidic screening the droplets of a flowing emulsion, the method comprising: flowing the emulsion alongside a continuous, non-emulsive stream of a second fluid to provide an interface between said emulsion and said stream of second fluid to cause said droplet to coalesce with said stream of second fluid; and detecting a property of said droplets of said flowing emulsion prior to said droplets flowing past said interface; and selectively incorporating the contents of said droplets of said flowing emulsion into a continuous microfluidic stream of said second fluid; and wherein the method further comprises selectively directing the trajectory of a said droplet responsive to said detecting to thereby selectively coalesce said droplets of said flowing emulsion with said second stream responsive to said detecting.

Techniques such as those described above facilitate the implementation of very high throughput combined micro-droplet-microfluidic processing systems.

The skilled person would understand that in implementations of the above-described techniques the contents of the droplet may comprise a very wide range of materials, but in some preferred implementations the contents include at least one insoluble object such as a crystal or, more particularly, a solid support such as a bead or microsphere. The techniques each droplet may contain no more than one such insoluble object; this facilitates processing and analysis.

One particularly advantageous process which is enabled by implementations of the above-described techniques is use of the second stream to perform some active function in processing or analysis of the contents of the droplets. Thus a composition of the second fluid may be employed to perform a biological or chemical operation on the contents of a droplet, for example to quench a chemical reaction, to maintain cell life or to lyse a cell.

A microfluidic device for accessing the contents of a droplet of an emulsion in a microfluidic system, the apparatus comprising: a flow cell, said flow cell having: a first microfluidic entry channel and first microfluidic exit channel for flowing said emulsion through said cell; a second microfluidic entry channel and second microfluidic exit channel for flowing a stream of second fluid through said cell, and wherein, in operation, an interface is formed in said cell between said emulsion and said stream of second fluid, and wherein said device further comprises a system to cause said droplet to coalesce with said stream of second fluid; whereby said contents of said droplet in said second stream are accessible from said second stream of fluid from said second microfluidic exit channel.

Preferably the system comprises means for applying an electric and/or magnetic field (which may include, for example, means for focussing a laser light on the interfaceA pair of electrodes may be provided for applying a lateral electric field across the interface between the stream of emulsion and the stream of second fluid.

A microfluidic system comprises:

an emulsion input to receive a stream of emulsion comprising a plurality of droplets of a dispersed phase of said emulsion in a continuous liquid phase; a second input to receive a continuous, non-emulsive stream of second fluid; a system for selectively merging a droplet into said continuous stream of second fluid responsive to a content of the said droplet; and a microfluidic output to provide said stream of second fluid including the contents of a said droplet to a microfluidic analytical device.

In implementations of the system the output stream of second fluid is substantially free of any components of the continuous phase of the emulsion, preferably at least as a dispersed phase that is substantially free of oil. (A small amount of the continuous phase of the emulsion may be present as a further laminar flow alongside the stream of second fluid, but, if present, this is easily separated from the stream of second fluid). The system may include the analytical device, optionally integrated on a common microfluidic platform with the droplet contents extraction system.

Preferably the system includes means for selectively coalescing droplets with the stream of second fluid, for example either by selectively directing a droplet onto the stream by an electric/magnetic field or by providing a system to selectively direct a droplet down one of a plurality of microchannels for later coalescing with the second stream.

Broadly speaking implementations of a microfluidic system as described above, may have a microfluidic channel with at least one dimension less than 1 mm, typically of order 10 μm to 500 μm. A microdroplet is generally less than 500 μm, 200 μm or 100 μm, for example in the range 20 μm to 100 μm, although microdroplets might be generated down to a dimension of order 1 μm (or even less). Generally speaking microfluidics are characterised by low Reynolds numbers, typically much less than one, this reflecting the relatively low importance of inertia compared with viscose and surface effects, and hence the substantially laminar flow that results.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

We will describe a technology that bridges the fields of microdroplets and continuous flow microfluidics by extracting on-chip the contents of microdroplets and incorporating them into a continuous stream. The extraction is achieved through electrocoalescence: droplets are forced to coalesce with an aqueous stream by applying an electric field across the channel. The extraction is controlled through the voltage applied at micro-fabricated electrodes on each side of the channel and can be performed in a continuous or discrete fashion. The discrete collection of droplets can be triggered by an external electrical signal. Interestingly, this signal can be related to the contents of the droplets. As a proof of principle, we have implemented a fluorescence intensity-based detection system to control the collection of the droplets, resulting in a device capable of selectively incorporating the contents of droplets of interest to a continuous microfluidic stream.

We use flow-focusing to generate microdroplets (S. L. Anna, N. Bontoux, H. A. Stone, *Appl. Phys. Lett.* 2003, 82, 364). An aqueous stream is focused between two oil streams as they pass through a junction. Shear forces make the aqueous thread break up into mono-disperse droplets. Droplet size and frequency are controlled by a combination of channel dimensions and flow rates. We use a mixture of fluorous oil (FC-77) and 1H,1H,2H,2H-pertluorooctanol (70:30 by weight) as the carrier phase. The oil and aqueous flows at the flow-focusing device are adjusted to generate the desired droplet frequency, typically ranging from 10-250 Hz. The flow of a lateral aqueous phase is adjusted so an interface is held in the region between the electrodes but no overflow in either direction occurs.

Figure 1C:
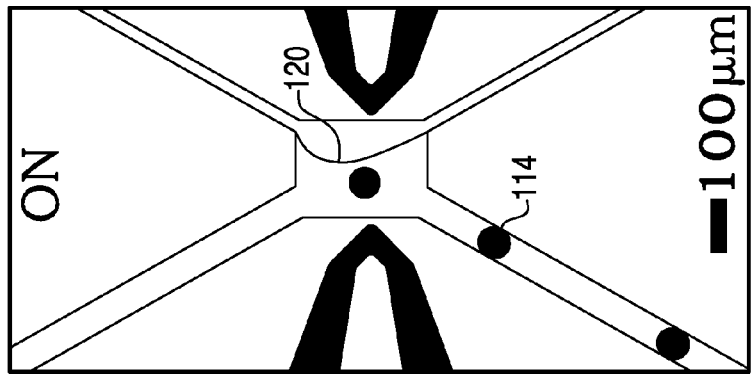
FIGS. 1a, 1b, and 1c show, respectively, a view from above of a microfluidic device for selective emulsion separation according to an embodiment of the invention, and micrographs illustrate the device in operation.
Figure 1B:
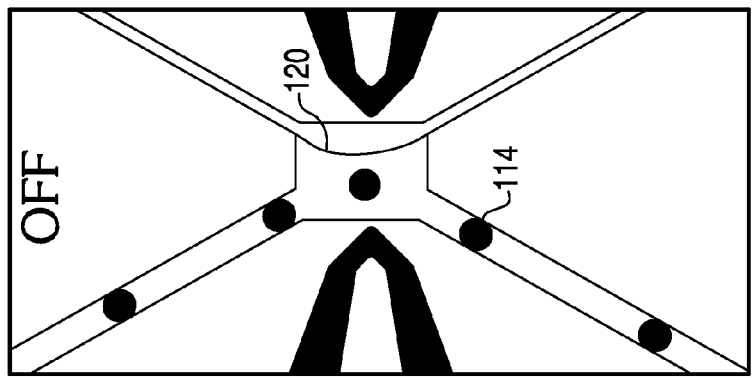
Figure 1A:
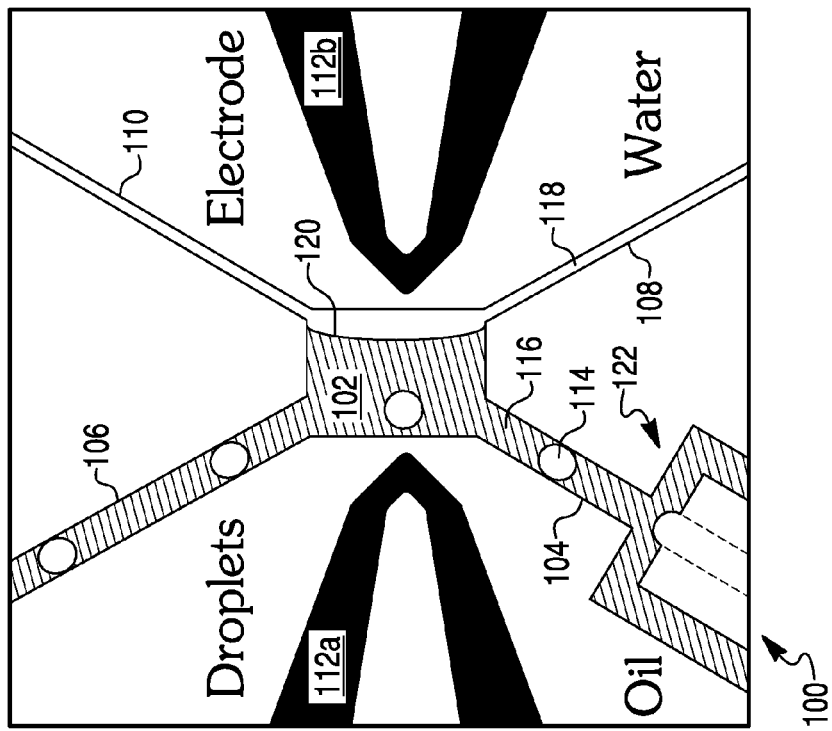

Referring now to FIG. 1a, this shows a microfluidic device 100 according to an embodiment of an aspect of the invention. The device comprises a chamber 102 with a first inlet 104 and first outlet 106 for a stream of emulsion and a second inlet 108 and second outlet 110 for an aqueous (water) stream. A pair of electrodes 112a, b are located to either side of chamber 102 to apply a lateral electric field to the flows within the chamber. FIG. 1a shows the device in operation illustrating droplets 114 of an aqueous solution being carried by an oil emulsion 116 through chamber 102 by channels 104, 106. At the same time a second stream of aqueous solution 118 is carried through chamber 102 by channels 108, 110, thus forming an interface 120 between the oil 116 and the aqueous solution 118 within chamber 102. In the illustrated example the droplets 114 are generated by a flow focussing device 122, but the skilled person will understand that many other techniques may also be employed to generate the emulsion, for example a microfluidic T-junction.

We used soft lithographic techniques to fabricate polydimethylsiloxane (PDMS) microfluidic channels and oxygen plasma to seal the channels with PDMS coated glass slides (see, for example, Y. Wang, H.-H. La, M. Bachman, C. E. Sims, G. P. Li, N. L. Allbritton, *Anal. Chem.* 2005, 77, 7539). Solder electrodes were fabricated using microsolidics (see, for example, A. C. Siegel, D. A. Bruzewicz, D. B. Weibel, G. M. Whitesides, *Adv. Mater.* 2007, 19, 727). Extra channels for the electrodes were included in the mold used to fabricate the fluidic channels. After the plasma treatment, the devices were placed on a hot plate at 130° C. (solder melting point 60° C.). When the device temperature had equilibrated, we introduced solder rods in previously punched holes, filling the cavity completely with solder by capillarity. Before removing the device from the hotplate, while the solid was still liquid, we introduced copper wires in the solder channels to serve as electrical contacts. Our typical device presents 50 µm wide channels for droplet formation and a 20 µm wide channel for the lateral stream. The channel in the electrode area is 170 µm wide, with the electrodes 10 µm from the walls. Channels are 25 µm deep.

In operation droplets generated on-chip flow parallel to a stream of water between two electrodes. In the absence of an electric field, the droplets are not perturbed by the presence of the aqueous stream and follow the geometrically determined flow lines. FIGS. 1b and c show micrographs of such a device in operation. Droplets of a dye generated at the flow focussing device flow past the electrode region on the absence of a field (b) whereas they coalesce with the lateral stream when a field is applied (c). As a result the dye contained in the droplets is transferred from its discrete carriers into a continuous stream.

In FIG. 1 b, in the absence of an electric field, droplets of a dye (Fe(SCN)$_x^{(3-x)}$ 67 mM) flow past the electrode region without interacting with the aqueous stream. FIG. 1c shows the collection of droplet contents. In the presence of an electric field, droplets coalesce with the lateral aqueous stream as they enter the electrode region and the dye contained in them is transferred to the stream. In this example the droplet frequency was ~240 Hz, the applied voltage in FIG. 1c was 2.3 kV.

In general, coalescence occurs when two or more interfaces approach below a critical distance, in the order of hundreds of nanometers, for a sufficient length of time. The critical distance and time depend on the chemical nature of the system and its dimensions. Electrocoalescence follows the same general mechanism but is modified due to electric forces appearing at the interfaces. When a voltage difference is applied to the electrodes an electric field in the direction perpendicular to the flow is created. This field is capable of altering the trajectory of the droplets and of polarising the interfaces. Above a threshold voltage, these effects can induce coalescence between the droplets and the aqueous stream.

In our experiments, typical voltages required to induce 100% coalescence ranged from 1.5 to 3 kV. Coalescence starts to occur at approximately 70% of the voltage necessary for total coalescence. These values of applied voltage generate an electric field of ~$10^7$ V/m. This relatively large electric field may be partially due to a larger distance between the interfaces (on the order of micros instead of tenths to hundreds of nanometers) and the short time of contact due to their relative motion (usually coalescing droplets are not moving with respect to each other).

We frequently observed a decay in the percentage of coalescence after establishing an electric field. One possible technique to address this problem is the use of pulsed fields, which have increased coalescence efficiency in bulk. A very interesting feature of using pulsed fields in a microfluidic environment is the ability to address individual droplets, as this provides a tool to access the contents of a single droplet on demand.

The above described technique employs an electric field to destablise the interface 120 between the oil and water but in other embodiments a magnetic field may be employed to de-stabilise this interface and hence facilitate coalescence. In still further embodiments de-stabilisation of the interface may be performed by focussing a laser on the interface.

Figure 2:
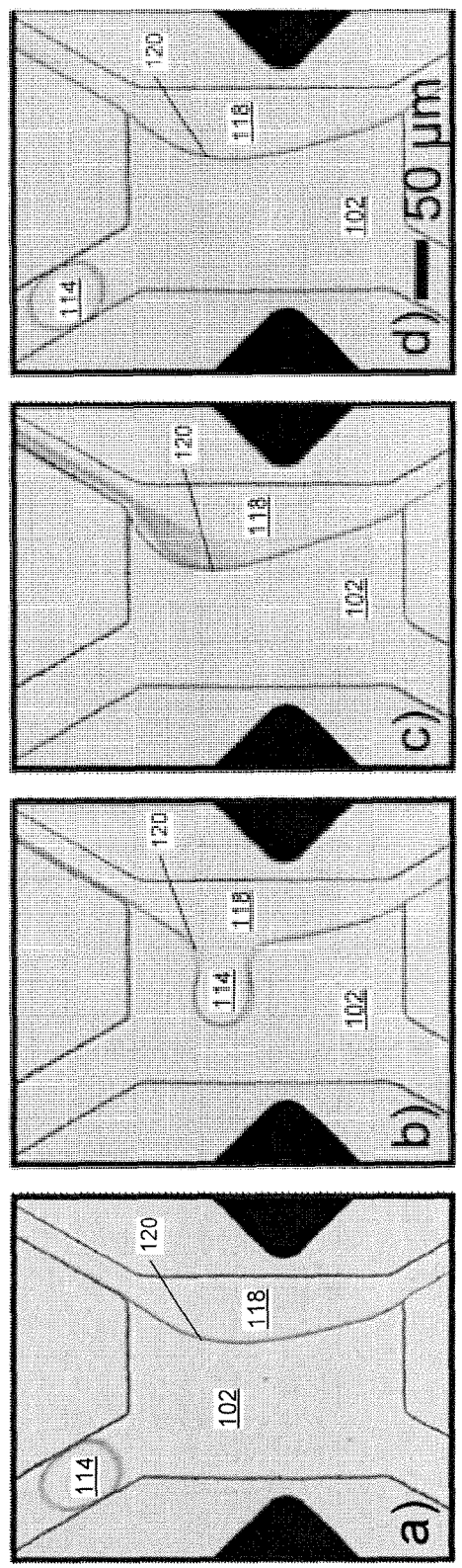
FIGS. 2a to 2d show a sequence of micrographs illustrating the extraction of the contents of an individual droplet.

FIG. 2 shows a sequence of micrographs where an individual droplet is selected from a stream. As shown in FIG. 2a, droplets flow past the electrodes when the applied potential (electric field) is insufficient for coalescence. When an additional square pulse is applied (FIG. 26), an individual droplet is selected and it is fused with its contents incorporated into the lateral aqueous stream. The applied voltage is then returned to its previous value before the droplet enters the electrode region and droplets then flow past again without coalescing. After the extraction, the contents of the droplet (in this example KSCN 0.8M) are incorporated into the aqueous lateral stream (Fe(NO$_3$)$_3$ 0.268M) and react with it, forming a coloured complex. To select an individual droplet it is important to ensure that only one droplet enters the region between the electrodes during the length of the pulse, therefore the pulse width and starting point must be carefully adjusted. In the illustrated example the droplet frequency was ~100 Hz, the pulse voltage 0.8 KV, the pulse width 10 ms and a baseline offset voltage of 2.5 KV was applied.

The pulses used to induce coalescence can be controlled by an external electrical signal. In order to demonstrate the potential of selective emulsion separation we chose to combine it with fluorescence intensity detection.

Figure 3:
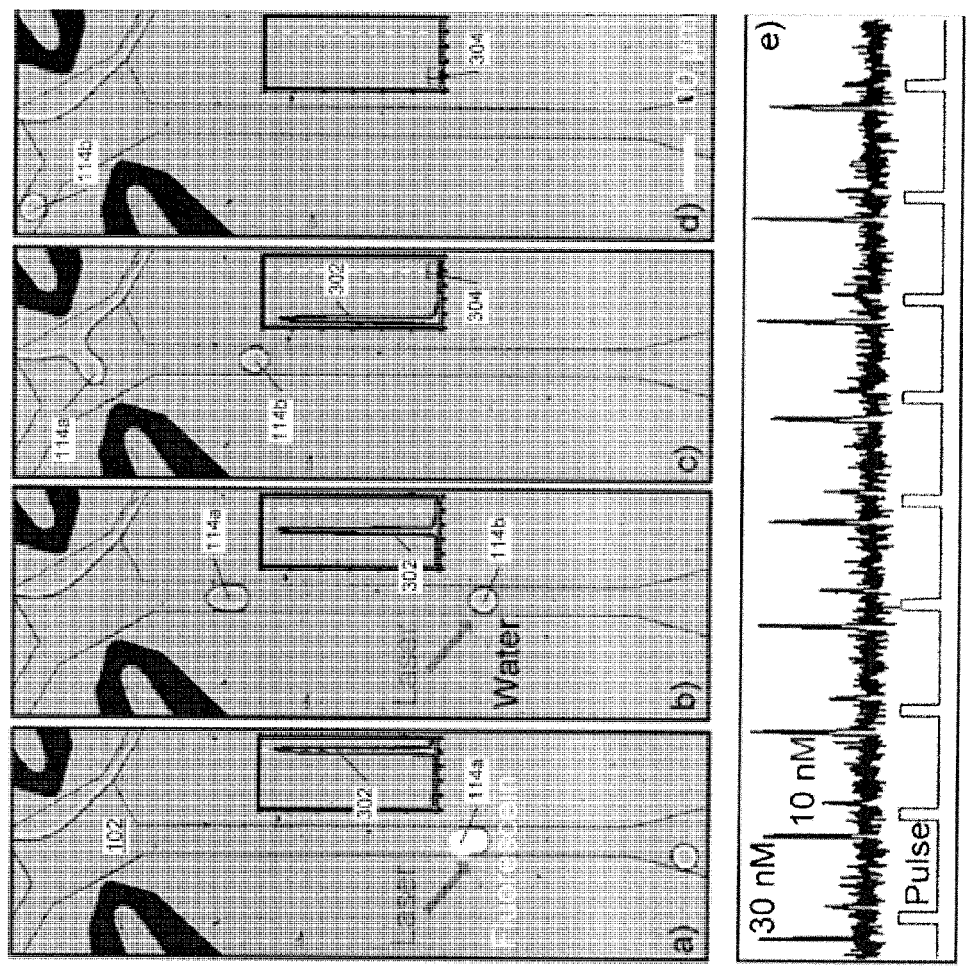
FIGS. 3a to 3f show, respectively a sequence of micrographs illustrating the selection and extraction of a fluorescent droplet of the device; a trace from a separate experiment illustrating the separation of droplets containing 30 nM fluorescein from droplets containing 10 nM fluorescein; and a schematic diagram of the microscope setup used.
Figure 3F:
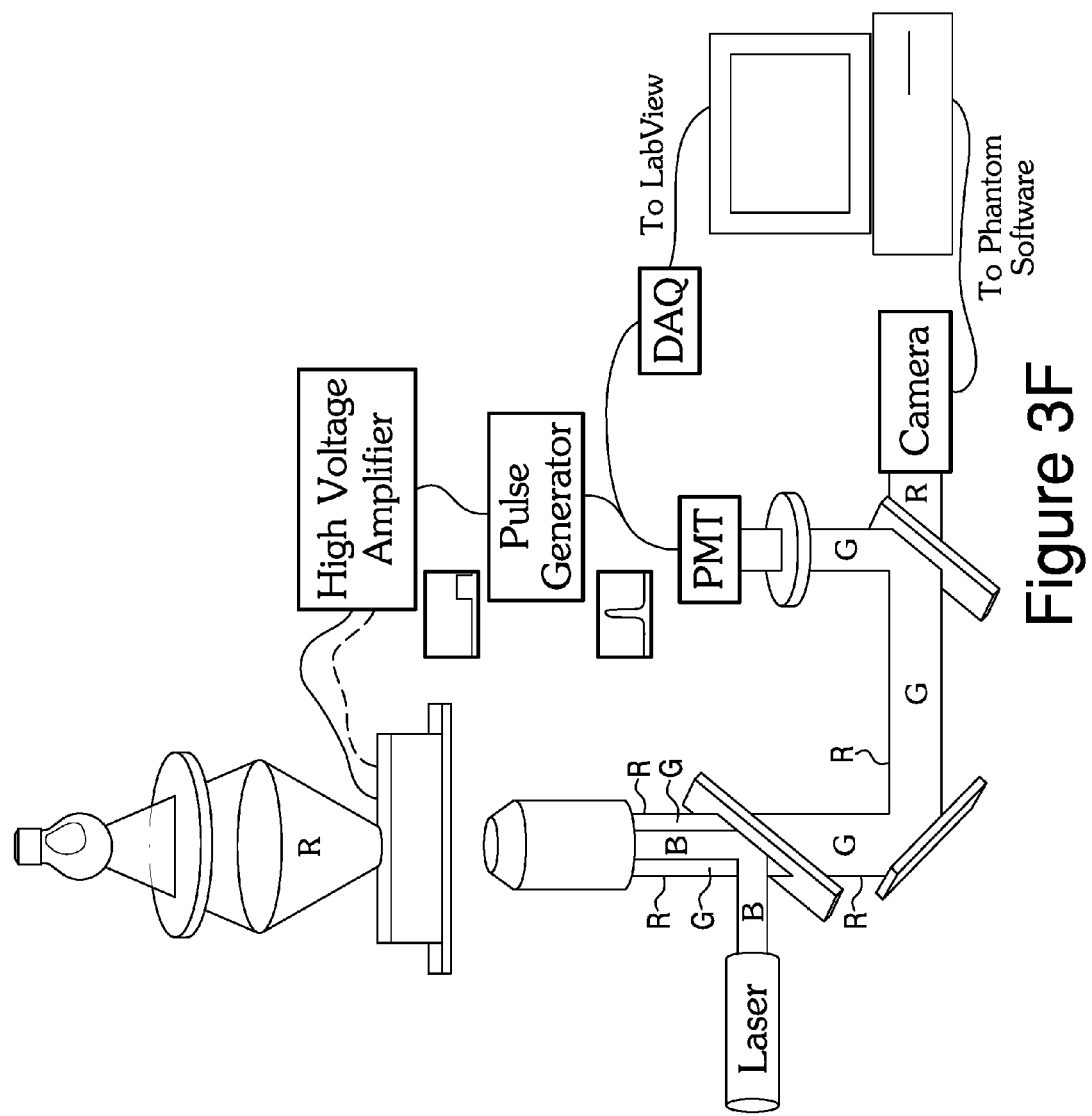

Using the level of fluorescence emitted by droplets to trigger the pulses we can discriminate them based on their contents. This discrimination can be used as the basis for selective emulsion separation in microfluidic devices. FIG. 3f shows the setup used, inter alia, to induce electrocoalescence based on fluorescence intensity detection (R, G and B refer to red, green and blue light respectively in this example figure).

Referring to FIG. 3f, the setup is based around an Olympus IX70 inverted microscope. The illumination light for imaging the device is filtered and focussed onto the device. Transmission images are obtained using a CCD camera (Phantom v7.2, Phantom Cameras, USA). For FIGS. 1 and 2 the illumination light is filtered using a green band pass (A52-535, Edmund Optics, UK) to increase contrast, while for FIGS. 3 and 4 (described below), a red long pass (A52-529, Edmund Optics, UK) is used to allow separation of the illumination light and emission of the fluorescein. In FIG. 2 where no fluorescent detection is used, the dichroic mirrors and PMT were not present and triggering of the pulse generator was performed manually. To achieve fluorescent detection, a 20 mW, 488 nm DPSS laser was coupled to the microscope via a long-pass dichroic mirror (FF500-Di01, Semrock, USA) which reflects the laser light into the objective while allowing the green emission light to pass through to the detection. A red-green dichroic (A47-423long pass, Edmund Optics, UK) is used to separate the illumination and emitted light and a 520 nm band pass filter is placed in front of the PMT to block non-fluorescein emission light. The output of the PMT is fed into the pulse generator and a DAQ card for recording. The generated pulses are amplified through a high-voltage amplifier connected to the device.

In operation the detector (photomultiplier tube, PMT) reads out a signal which is proportional to the fluorescence of the excited droplet. When the signal exceeds the threshold of the pulse generator trigger, a high voltage pulse is applied across the electrodes. The gain of the PMT can be adjusted to allow the triggering to take place at any level of fluorescence, with the signal-to-noise ratio determining the reliability. The use of a pulse generator allows the width and voltage of the pulse to be changed independently of the signal which triggers it.

FIGS. 3a to 3d show a sequence of micrographs where a fluorescent droplet is detected and fused while a non-fluorescent droplet flows past the electrodes undisturbed. Using a device comprising of two separate flow focusing devices we generated a stream of alternating fluorescent and non-fluorescent droplets. When the fluorescent droplets flow past the laser the emitted light is gathered by the detector whose signal triggers a pulse that induces coalescence. Non-fluorescent droplets do not trigger a pulse and therefore are not incorporated into the lateral stream. The laser detection point is arbitrarily chosen, and a time delay between the detection and the pulse is introduced to account for the distance the droplets have to cover between the laser and the electrodes.

In more detail, insets shows 10 ms of signal 302 from the detector and signal 304 from the pulse generator with the current frame position marked with a vertical dashed line. In FIG. 3a, a droplet 114a containing 12 mM fluorescein flows through the laser spot and emits fluorescent light which is detected by the PMT; in FIG. 3b a water droplet 114b passes through the laser spot without fluorescing. In FIG. 3c, an electric pulse across the electrodes causes the droplet 114a containing fluorescein to merge with the lateral stream. In FIG. 3d the field is removed before the water droplet 114b passes between the electrodes so it flows past. FIG. 3c shows the trace from a separate experiment showing the signal from the PMT (upper) and pulse generator (lower) for a stream of droplets (frequency ~80 Hz) containing 30 nM and 10 nM fluorescein droplets, showing that only the droplets containing 30 nM fluorescein trigger the pulse generator (pulse details: voltage 0.5 kV, width 2.5 ms, delay 3.5 ms, offset voltage 1 kV).

These experiments demonstrate that: the duration of reactions can be accurately controlled (start time and flow rate i.e. elapsed time are well-defined), droplet formulation is carried out using microfluidic techniques, and the contents of the target droplets are extracted on-chip allowing further processing. For high-throughput screening, it is generally important to be able to select droplets containing low concentrations of fluorophores from an array of concentrations very similar to the target. To demonstrate the capability of this system for such studies we selected droplets containing 30 nM fluorescein from a stream that contained droplets of 30 and 10 nM concentration. FIG. 3 (e) shows the trace of successful pulse triggering for droplets containing 30 nM fluorescein whereas droplets 10 nM in concentration do not trigger pulses. Analysis of a larger sequence of the trace (not shown) shows that all 30 nM and less than 1% of the 10 nM droplets were selected. The lower limit of fluorescein concentration for successful triggering in our experiments was 15 nM, beyond which the signal-to-noise ratio was too low to trigger the pulses reliably. The noise in our system was due to the illumination light used to capture the videos and ensure selection was taking place. If visual confirmation of the selection process was not required, the signal to noise should be substantially improved.

Solid supported chemistry and biochemistry plays an important role in biotechnology, drug discovery and combinatorial chemistry. Our techniques allow combining solid supported chemistry such as microspheres/beads and microdroplets in a microfluidic environment, in particular for higher-throughput technologies. We used selective emulsion separation to detect and extract fluorescent beads encapsulated in microdroplets and incorporate them into a continuous microfluidic stream. These techniques may also be extended to assays performed on fluorescence reporting beads as well as cell-based assays.

The localisation of fluorescence on the beads makes detection more difficult. If a fluorescent bead and the excitation laser do not overlap as the droplets passes, there will be no fluorescence, despite the present of the bead. To counter this problem the excitation laser beam is expanded in order to excite the entire droplet. The laser focus is not uniform across the droplet, and hence the signal recorded from the PMT is dependent on where the bead is relative to the laser.

Figure 4:
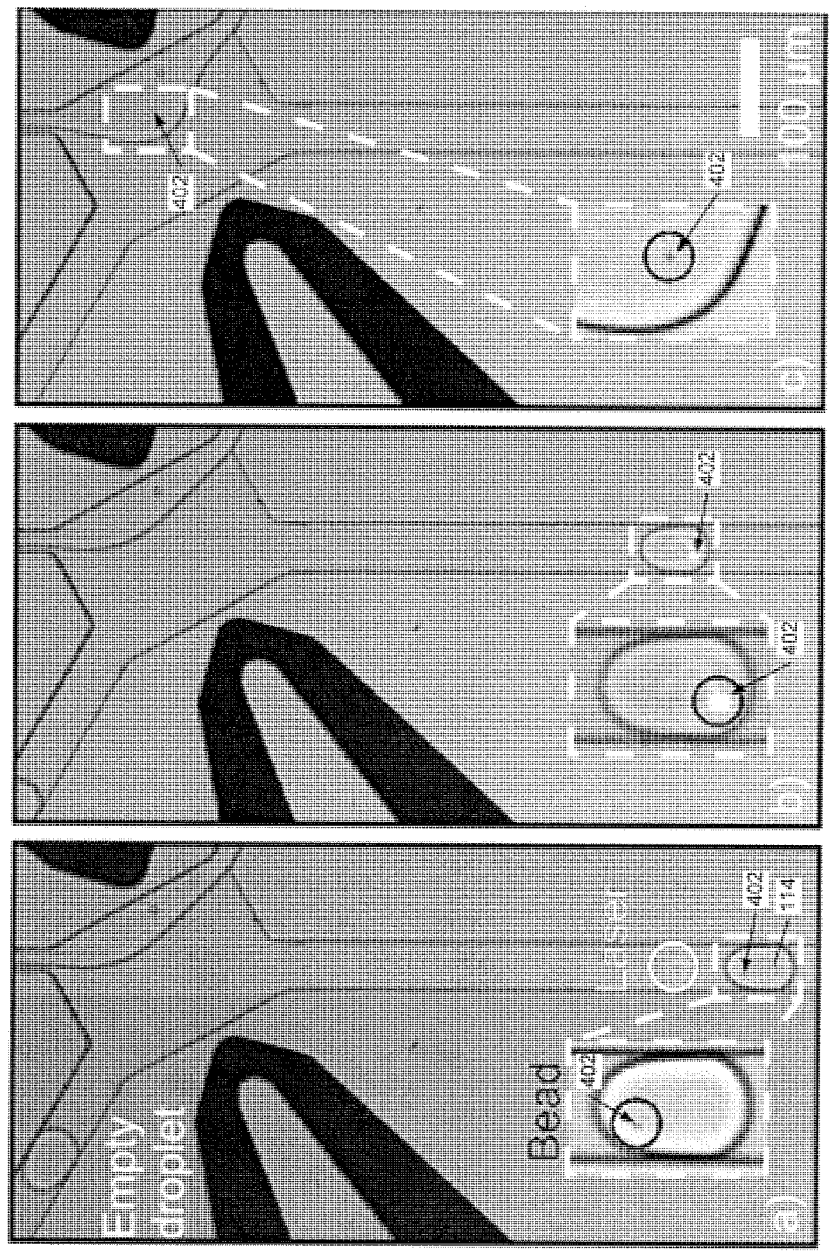
FIGS. 4a to 4c show a sequence of micrographs illustrating the selection of a droplet containing a fluorescent bead.

To study the selection of bead containing droplets, we generated droplets of a solution containing 2 µm diameter fluorescent beads (0.005% (v/v)) in phosphate buffer. This concentration results in ~$10^4$ beads/µl. With an approximate droplet volume of 50 pl, the number of beads per droplet is ~0.6. This resulted in most of the droplets containing either one or no beads. The fluorescence intensity emitted by the beads was used, as previously, as the signal to trigger a high-voltage pulse. FIG. 4 shows a sequence of micrographs where a droplet containing a fluorescent bead is selected and merged with the lateral stream. The bead can be seen both inside the droplet before fusion (FIGS. 4a, b) and within the stream after fusion (FIG. 4c).

We have described examples of techniques which use an electric field to coalesce a droplet of an emulsion with an aqueous stream. However, the inventors have determined that use of an electric field is not essential, which is helpful because although the above-described techniques perform well at a droplet frequency of 1 Kz, at frequencies of the order of 10 Kz the droplets are so close together that such electric field based techniques can be difficult to employ effectively. In such cases a high throughput screening may be performed in a different, albeit related manner, as selecting droplets of interest in a first, upstream stage to direct only the selected droplets into a microchannel and then coalescing all the droplets in that microchannel with a second, aqueous stream. This is illustrated schematically in FIGS. 5a and 5b which illustrate microfluidic screening apparatus 500 comprising a first, selection stage 502, and a second, droplet merger stage 504. In the first, selection stage 502 a droplet 114 is selectively directed into one of a plurality of microchannels 502a, b, for example by detecting fluorescence and applying an electric field. The skilled person will, however, be aware of many other techniques which may be employed in this stage. Although only two streams are illustrated a large library of items for analysis may be divided into many different streams, either at a single junction or using a tree structure.

Figures 5A, 5B:
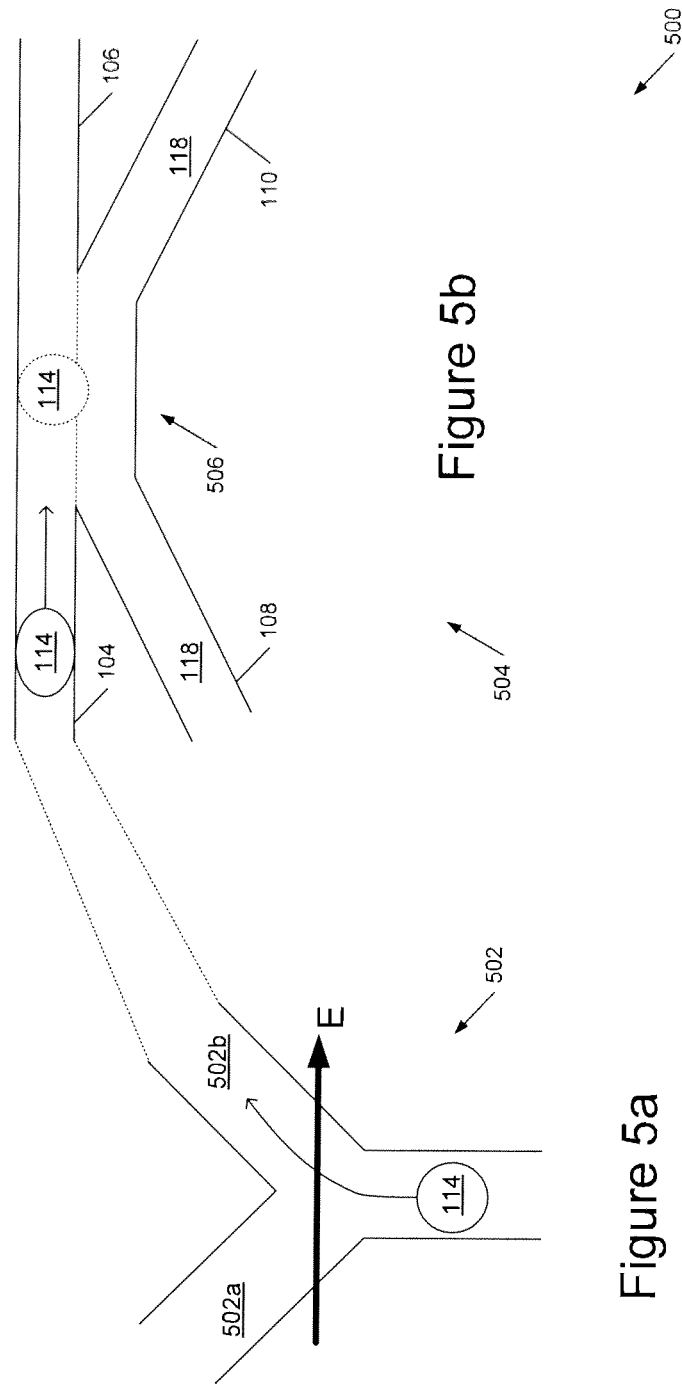
FIGS. 5a and 5b show, schematically, microfluidic screening apparatus with separate regions for selective emulsion separation and droplet-stream coalescence according to a second embodiment of the invention.
Figure 6:
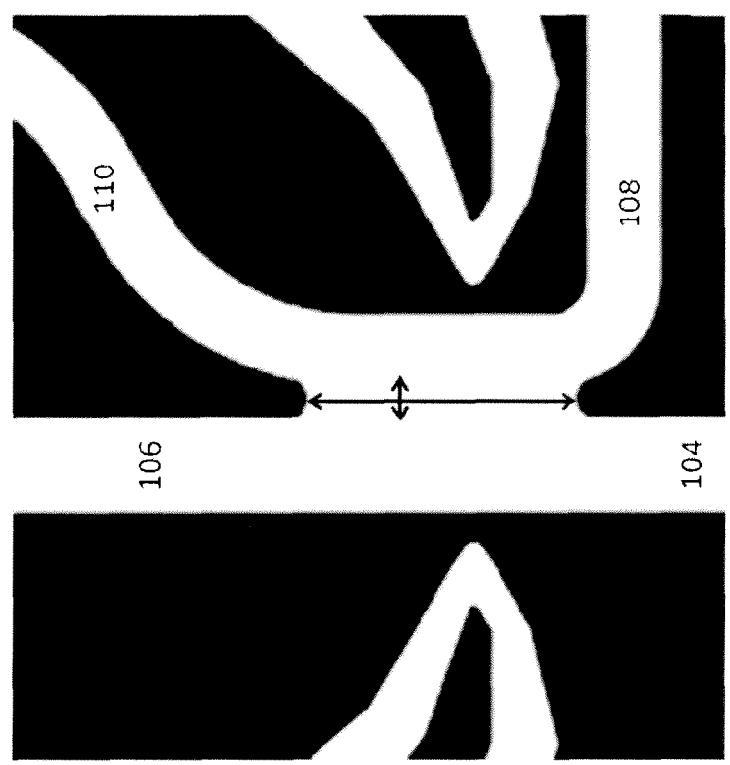
FIG. 6 shows microfluidic channels and electrodes.

These stream of selected droplets, in the illustrated example contained within microchannel 502b are then all merged with an aqueous stream 118, in the illustrated example using a geometric technique in which the microchannel 502b is narrowed to confine a droplet 114 in at least one dimension until the droplet is allowed to expand into a chamber 506 where surface forces bring the droplet towards a more symmetrical (spherical) shape thus de-stabilising interface 120 and causing a droplet 114 to merge with the laminar flow of aqueous stream 118. The skilled person will appreciate that FIG. 5b illustrates one example of a geometry which will cause droplet 114 to merge with stream 118, but the skilled person will appreciate that other geometries are possible.

One important advantage of the above-described techniques is that they facilitate the combination of microdroplets-based techniques with microfluidic analytical devices. In general microfluidic analytical devices will not work satisfactorily with a stream of emulsion as oil affects the operation of such devices. The above described techniques enable the contents of a droplet to be separated from the oil so efficiently that the resulting stream of aqueous solution is as if the materials carried by the solution have never been in an emulsion in the first place. Further, the aqueous stream may be employed to functionally process the contents of a droplet, for example by cleaving a material such as DNA from a solid support such as a microsphere. The skilled person will appreciate that the above techniques may be employed for a very wide variety of chemical and biological procedures including, but not limited to, the processing and analysis of DNA, proteins, cells, enzymes, antigens and the like, in particular, in high-throughput systems, as well for other chemical and/or biological reactions and processes, for example PCR (polymerase chain reaction), and in a wide variety of sensors and detectors, for example for detecting biological, chemical or radiological threats.

In summary we have demonstrated technology capable of extracting the contents of microdroplets on-chip and incorporating them into a continuous microfluidic stream. We are able to select individual droplets based on their contents. As a proof of principle, we have implemented a fluorescence detection system and used it to collect droplets containing low levels of a fluorescent dye as well as single fluorescent beads. This technology enables many applications, for example in the fields of directed evolution, enzyme inhibition studies, high-throughput drug screening, and more. This device has the potential to combine all of the available microfluidic techniques with microdroplet based screening. Moreover, further control can be provided by adjusting the composition of the receptor stream. This stream can be used to quench reactions so that their endpoints are accurately determined, ensure that cells do not encounter any adverse environments or, on the other hand, lyse cells to study their contents on-chip after a reaction carried out in droplets.

In the case of microspheres or microbeads, these may be used to carrier a biological material such as DNA, which may afterwards be cleaved off the solid support in or downstream of the second stream for further processing and/or analysis.

Preferred Embodiments

The inventor has realised that different angles of the flow cell design may influence drop flow in any of the above aspects and embodiment, for example behaviour of the droplets as the flow rate increases. The design may therefore impact reliability of coalescence and/or selection.

A preferred embodiment of the flow cell, which may comprise any combination of any of the above-described aspects and optional features thereof, has a four-port chamber with channels, the flow cell having a shape which may be described as 'K'-shaped, for example as shown in FIG. 5b. Such a shape may allow a tangential approach of one flow to another substantially straight flow; this may be advantageous to help each droplet to merge into the second flow.

Preferably, both of the channels on respective input ports, and/or both of the channels on respective output ports, are of substantially equal width, for example substantially equal to the width of an undistorted droplet. The width of the chamber perpendicular to the direction of flow (substantially straight) of the second fluid is preferably greater than, e.g., substantially double, the width of the input channels and/or output channels at the ports. The substantially equal to the channel width to an undistorted droplet may be advantageous for ensuring one-by-one injection and/or collection of the micro droplets.

Where coalescence of micro droplets from a first fluid into a second fluid is required in the chamber of such a 'K'-shaped arrangement, the first fluid may flow along a substantially straight route through the back of the 'K'-shape, for example through channels 104, 106 following the directional arrow on the micro droplet 114 in FIG. 5b. Whereas the second fluid, generally an aqueous stream, flows along a curved path following the arms of the 'K'-shape, i.e., along the channels 108, 110 via chamber 506. Some of the first fluid may further flow into the output channel 110, however generally the first and second fluids remain unmixed in this channel and are thus easily separated. As described above, in operation a field may be applied to merge a micro droplet into the second fluid if fluorescence of the micro droplet content is detected. The field may be, e.g., an electric and/or magnetic field, e.g., with pulse width about 2.2 ms.

Another embodiment may comprise a four-port flow cell having for example a generally 'X' or 'H' shape. However, such embodiments, in particular the 'H' shape arrangement, are less preferred relative to the above K-shaped cell. However, any one of the K, X or H shaped arrangements may allow faster selective merging of a micro droplet into a second fluid and thus higher throughput, for example in comparison to a Y-shaped three-port arrangement. A cell throughput frequency of 60-70 Hz, i.e. droplets per second, may be achieved for example for relatively large droplets. Moreover, the K-shaped arrangement in particular may be advantageous for aiding coalescence, thus improving reliability and/or throughput of the micro droplets. Furthermore, it is noted that an H shape cell is generally less efficient.

Electrodes and/or laser source(s) for deflection of the microdroplet may be arranged adjacent the chamber similarly as for the above-described embodiments.

Regarding microdroplet content detection, light source and receiver apparatus, e.g., optical fibres, may be placed for example on opposite sides of a channel to excite and detect fluorescence of micro droplets, the exciting of the fluorescence preferably using ultraviolet and/or laser light. For increased sensitivity, the fibers are positioned close to the channel. Additionally or alternatively, the excitation light may be provided from above a microfluidics chip comprising the channel (e.g., using 'plif': portable laser induced fluorescence), and an optical fibre for detection provided below in conjunction with a photomultiplier tube.

The light source and receiver for the excitation and detection respectively, e.g., the above optical fibres, may advantageously be offset along a direction of micro droplet flow. Such spatial separation of the excitation and detection fibres along the flow direction provides for a delay between excitation and detected fluorescence. This may allow a time-resolved assay, for example implementing a time delay of the order of microsecond(s) or more between excitation and detection. Advantages of such a delay may be understood by consideration of the long half-lives of, e.g., lanthanide metals (e.g., up to about 1.5 ms), and that, in an example implementation, when a sample is flashed with an excitation laser, any proteins will generally fluoresce at the same time. Such 'background' fluorescence may be avoided during a delayed detection of fluorescence of the contents of the microdroplet under test, e.g., cell, antibody, etc.

Even a relatively small spatial separation may be advantageous, taking into account the angle of divergence of the light exiting the source, e.g., about 9 degrees from the optical axis of the source optical fibre, and corresponding collection angle of the receiver. By spatially separating the fibres, the ends of which are preferably cut substantially flat (i.e., across the fibre cross-section) to facilitate increased sensitivity when placed close to the channel, direct entry of the excitation light from the source into the receiver may be reduced or even avoided, thus improving the signal-to-noise ratio of the detection signal.

Additionally or alternatively, the source and receiver, e.g., optical fibres as above, may be arranged to output and collect light in different non-parallel directions. For example, the optical axis of a source optical fibre may be at an angle of 45 degrees or more, e.g., 90 degrees, to the optical axis of a receiving optical fibre.

Signal-to-noise ratio of the detection signal may be further improved by use of a filter to reduce entry into the receiver of light that does not result from the fluorescence in the micro droplet.

In an embodiment, including any aspect described herein, a field pulse applied to cause a droplet to merge into a second stream may be adjusted, e.g., by adjusting the timing of field pulse edge(s) and optionally also the magnitude of the field pulse, to distort a droplet, this advantageously leading to increased probability of merging of the droplet into the second stream. Thus, the time-domain shape of the electric and/or magnetic field applied to redirect the droplet may not be exactly rectangular, or may be not at all rectangular, e.g., may be substantially triangular or one half of a sinusoid. In particular, the shape may deviate from a rectangular pulse so that the droplet in the chamber distorts and touches the second (e.g., aqueous) stream. A selected droplet may then more reliably merge or coalesce into the second stream. For example, an electric field may applied as a pulse having reduced slew rate on the positive- and/or negative-going transitions/edges; indeed the slew rate of either Alternatively, the slew rate of either or both of the edge(s) may be such that the 'pulse' has a triangular shape. Advantageously, distortion by the field having slower slew rate(s), rather than, e.g., merely re-directing, may enhance merging of the droplet into the second, e.g., aqueous flow/stream. Such distortion, e.g., elongation, of the droplet may occur specifically during the reduced slew rate transition(s), so that for example a spherical droplet is distorted at the first, e.g., positive-going transition, and then returns to its spherical shape before or at the following, e.g., negative-going transition. In view of such distortion that may occur during a transition, the field applied for each droplet may additionally or alternatively comprise a series of fast pulses, with or without slew rate reduction.

Figure 7:
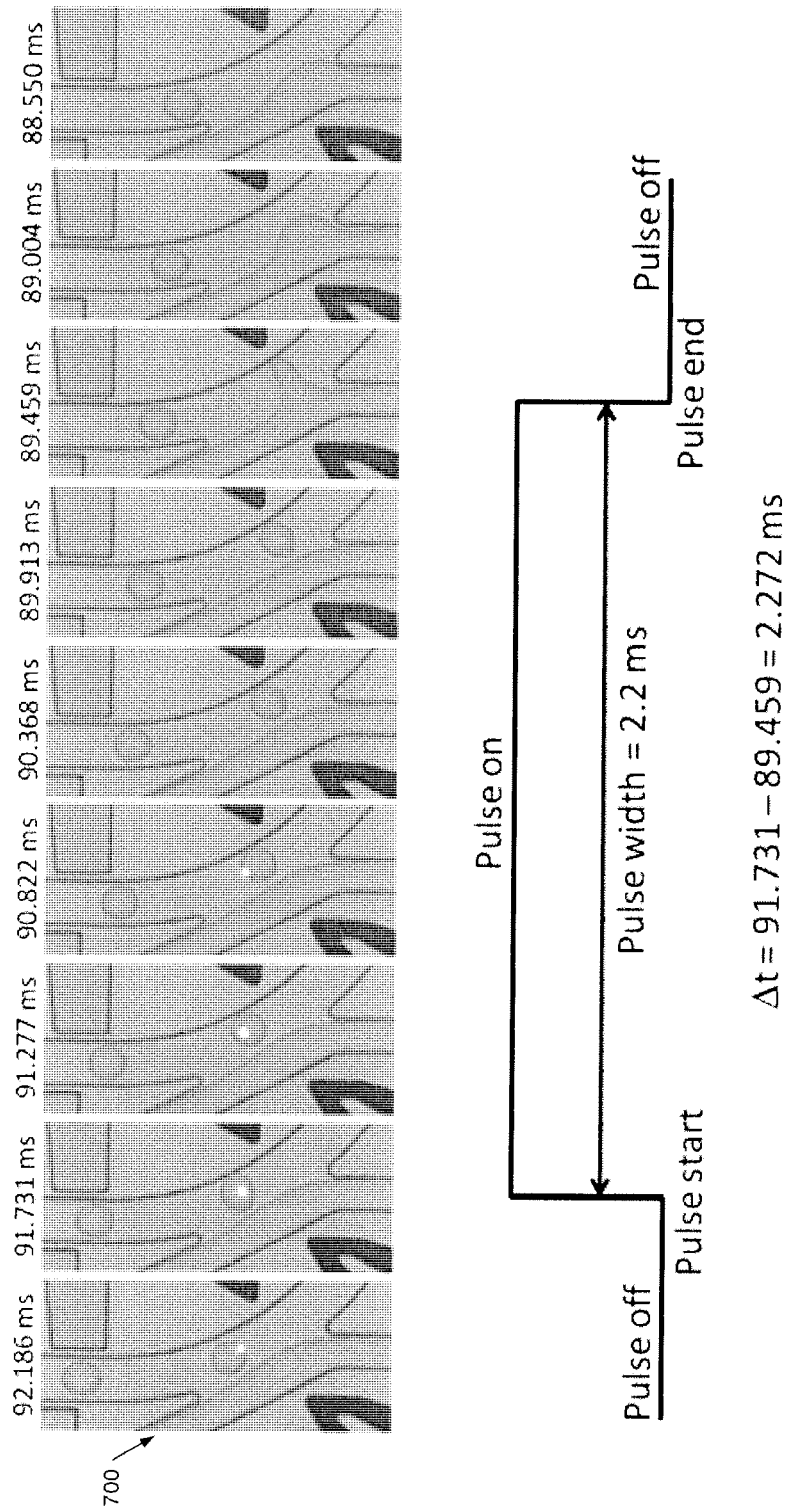
FIG. 7 shows droplet distortion by high electricity potential pulse.
Figure 8A:
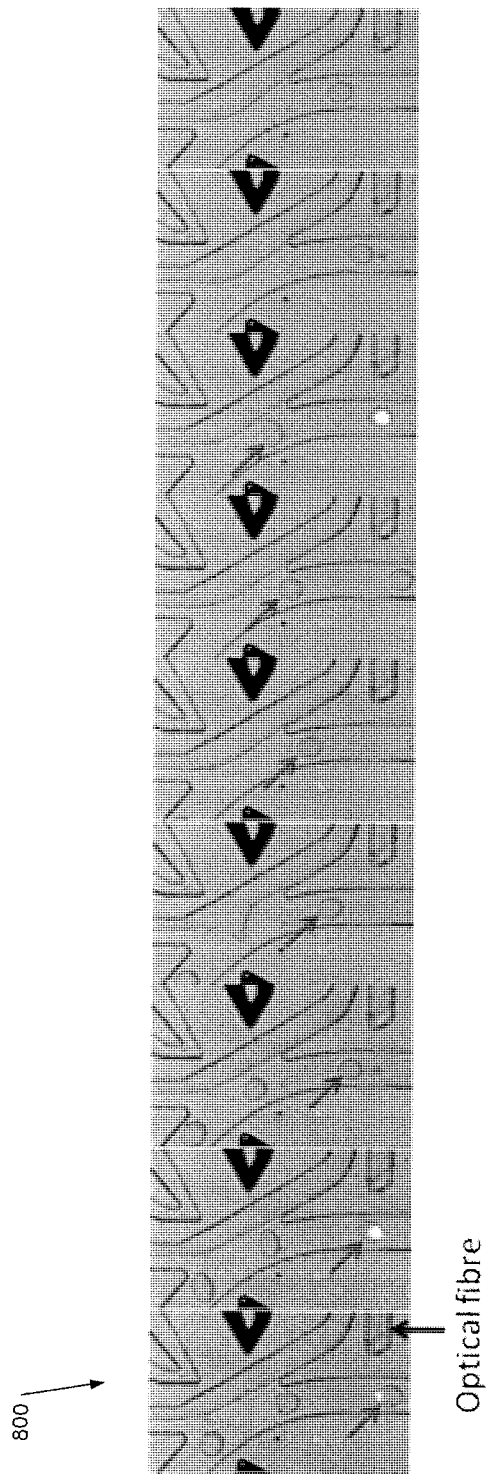
FIGS. 8a and 8b show use of an optical fibre for fluorescence detection.
Figure 8B:
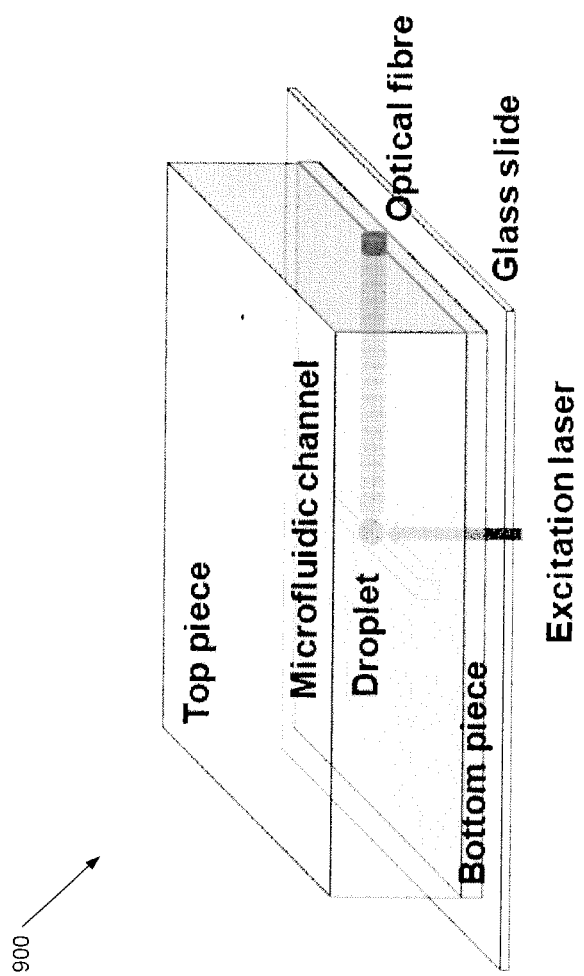

Regarding use of a flow cell as shown by the images and waveform of FIG. 7, surfactant-stabilized droplets of the said emulsion in the said continuous fluid phase flow into the said flow cell close to the said interface between the said continuous fluid phase in the first microfluidic channel and the continuous stream of the second fluid in the second microfluidic channel. An electricity potential pulse is applied between the two said electrodes if a fluorescent emission signal is detected in the said droplet in the said flow cell, and of an intensity exceeding set criteria. The electricity potential, which is applied between the two said electrodes, is within the range between 10 and 2000 volts, preferably between 100 and 1000 volts, and further preferably between 400 and 800 volts. The said droplet is elongated along the electric field lines between the two electrodes at the moment when the electricity potential alters from zero to the set value and from the set value to zero. The said droplet is elongated enough to contact with and break through the said interface between the said continuous fluid phase in the first microfluidic channel and the continuous stream of the second fluid in the second microfluidic channel so that the contents of the said droplet merges into to the said continuous stream of the second fluid in the second microfluidic channel.

The following concerns example implementations of embodiments for droplet based cell sorting.

Figure 12:
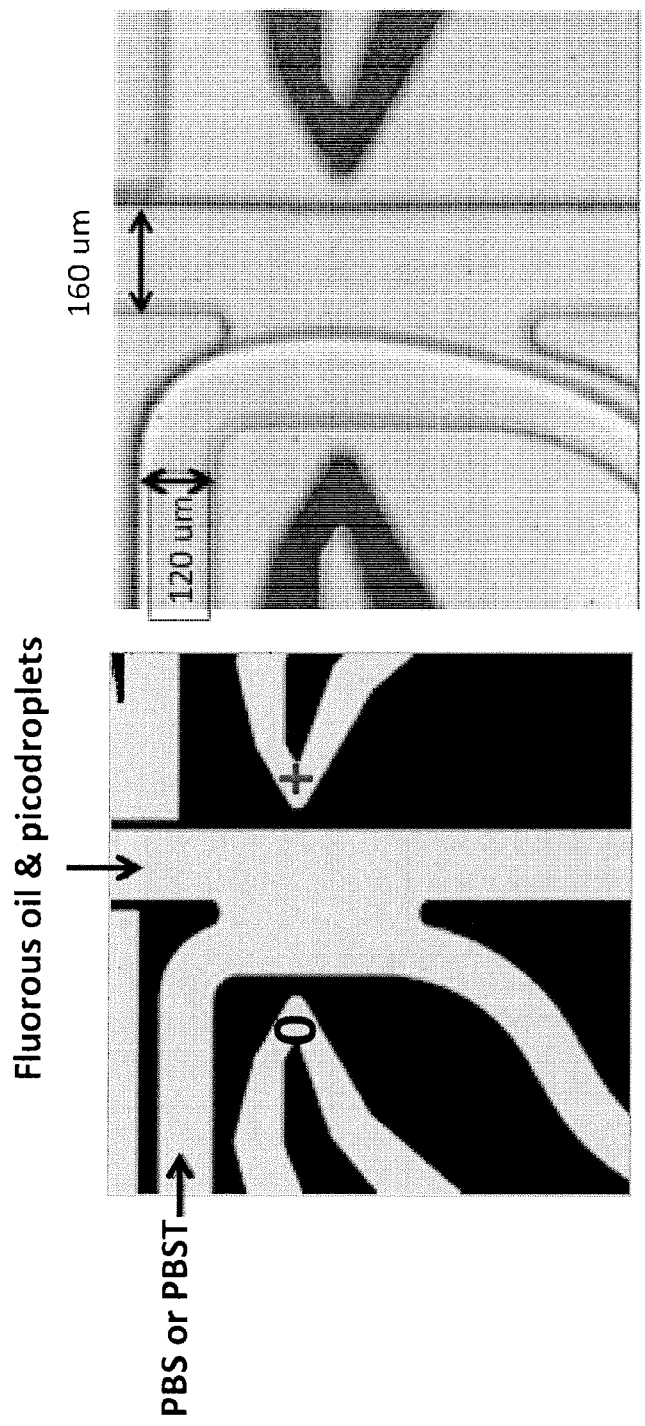
FIG. 12 shows a K chamber device.

FIG. 12 shows a K chamber device. The device has a 160 um fluorous channel, a 120 um aqueous channel and 75 um depth.

Figure 13:
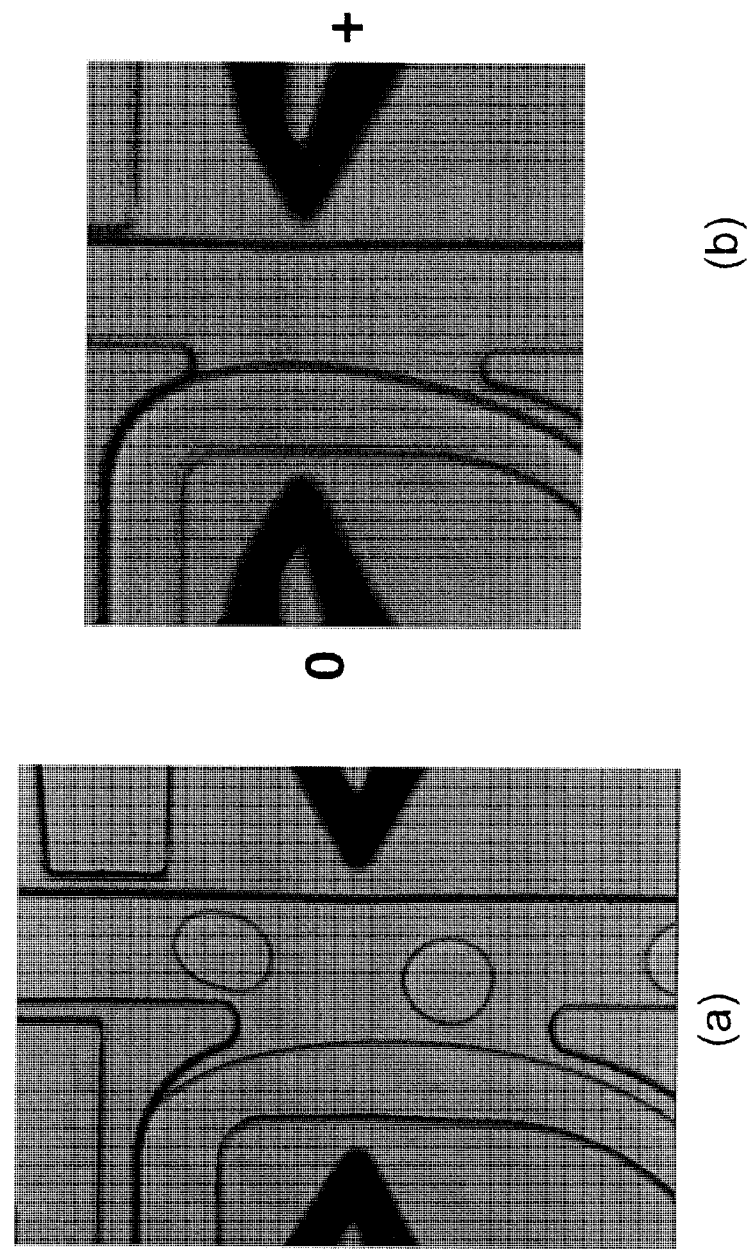
FIG. 13 shows: (a) drop injection in a k-shaped device; and (b) droplet separation in a k-shaped device.

FIG. 13(a) shows drop injection in a k-shaped device, implementation parameters being: fluorous carrier oil (HFE7500; 2×1125 uL/hr); aqueous carrier phase (PBST; 2500 uL/hr); droplet (2% PS-1, 121211-02; 109 um diameter, 677 pL volume; mixture (~1:1) of 1 uM AF488 labelled streptavidin in PBS and 200 nM AF488 labelled streptavidin in PBS; 500 uL/hr); and droplet injection frequency: ~110 Hz.

FIG. 13(b) shows droplet separation in a k-shaped device, implementation parameters being: fluorous carrier oil (HFE7500; 2×1350 uL/hr); aqueous carrier phase (PBST; 2500 uL/hr); droplet (2% PS-1, 121211-02; 109 um diameter, 677 pL volume; mixture (~1:1) of 1 uM AF488 labelled streptavidin in PBS and 200 nM AF488 labelled streptavidin in PBS; 100 uL/hr); pulse voltage: 440 v; pulse width: 3.68 ms; sorting frequency: 39 Hz.

A further example implementation of droplet mixture injection using a K chamber has implementation parameters being: (a) picodroplets comprising: 50 nM AF488 Goat anti-mouse IgG, light chain specific in PBS; 200 nM AF647 goat anti-mouse IgG Fc fragment specific in PBS; Positive: 50 nM mouse IgG; and/or Negative: 0 nM mouse IgG, and (b) injection parameters of: 160F 120A K chamber 75 um depth single layer device; 2×1375 uL/hr HFE7500; 2500 uL/hr PBS; 50 uL/hr picodroplets. The same parameters may be used for droplet mixture sorting based on a FRET signal, preferably however with 200 uL/hr droplet flow, and with a sorting pulse of, e.g., 480 v amplitude and 2.25 ms width.

Figure 14:
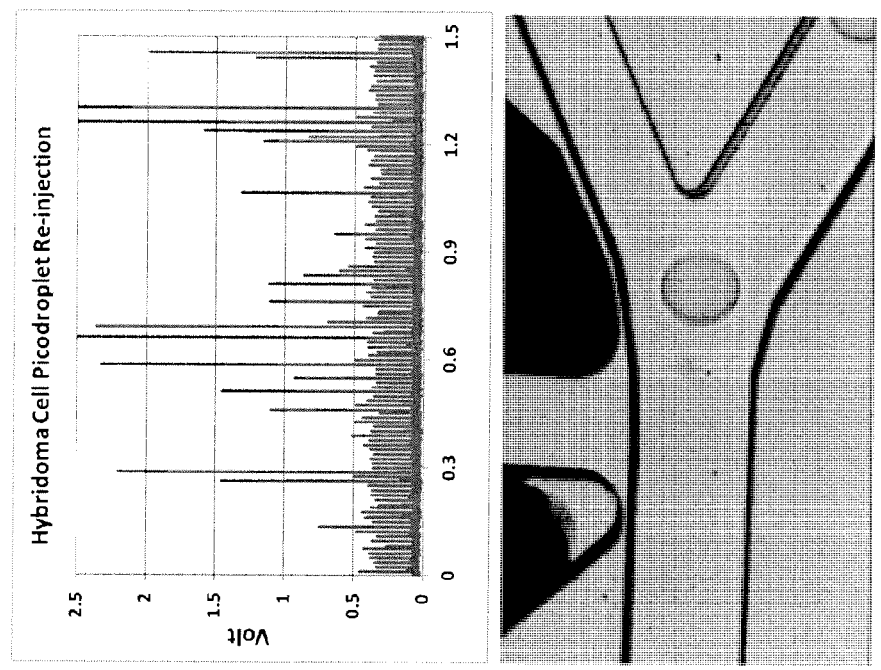
FIG. 14 shows a y-shape chamber for injection and sorting based on FRET signal.

An implementation using a y-shape chamber for injection and sorting based on FRET signal, as shown in FIG. 14, has implementation parameters being: Picodroplets (200 nM AF488 Goat anti-mouse IgG, Fc fragment specific; 50 nM AF647 goat anti-mouse IgG light chain specific; Washed hybridoma 528 cells in DMEM, 10% horse serum and 15% Ficoll, encapsulated with the above two reagents; Incubated at RT for 1 hr and 20 min; 109 um diameter, 667 pL); injection (picodroplet sorting design 133 um collection channel width, 75 um deep; 2×2000 uL/hr HFE7500; Droplets: 200 uL/hr); sorting pulse (640 v amplitude and 1.2 ms width; no delay); and frequency 89 Hz.

Figure 15:
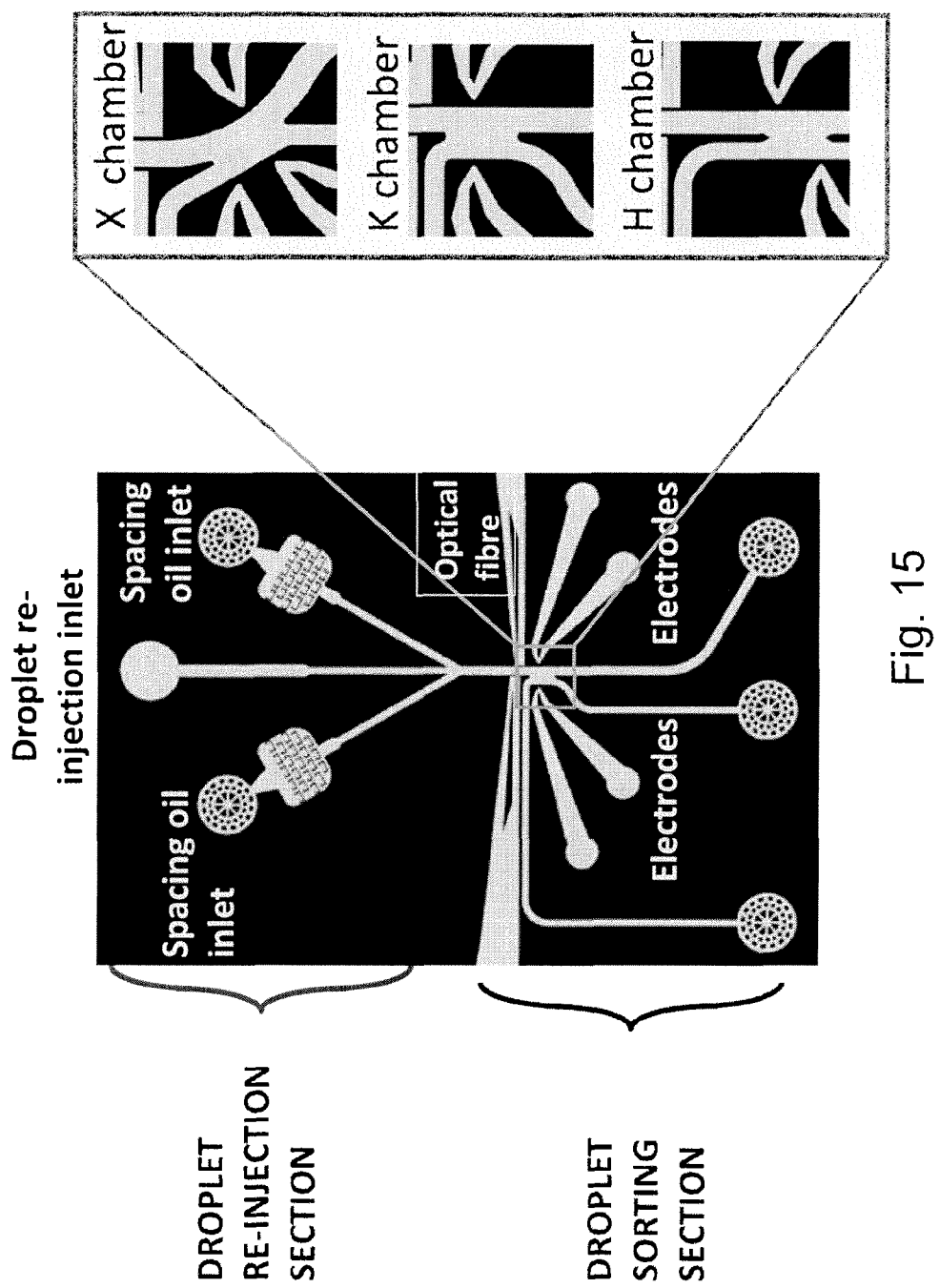
FIG. 15 shows de-emulsification designs.

De-emulsification designs are shown in FIG. 15.

Figure 16:
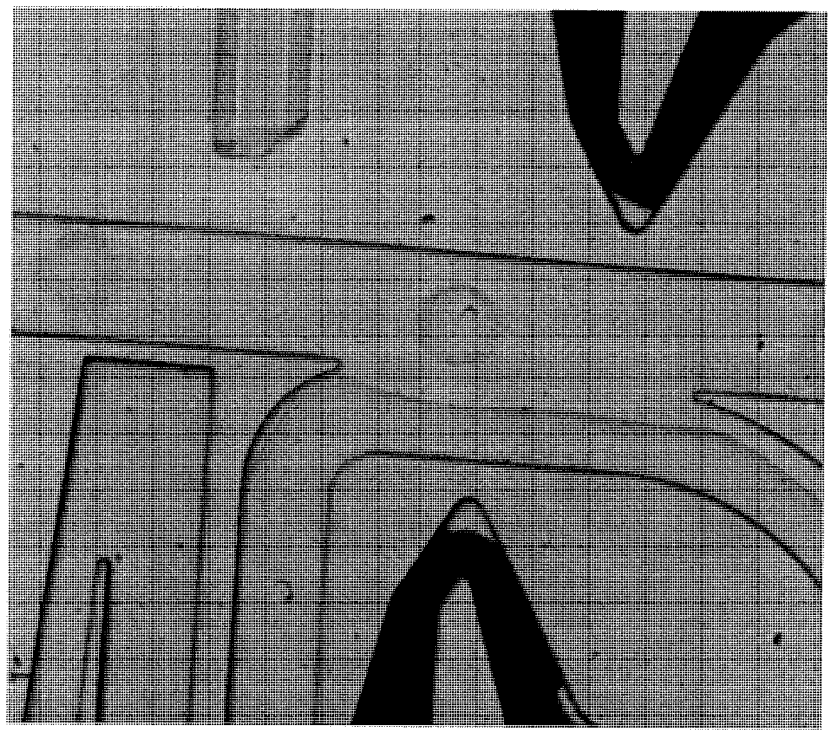
FIG. 16 shows an embodiment of droplet mixture sorting.
Figure 17:
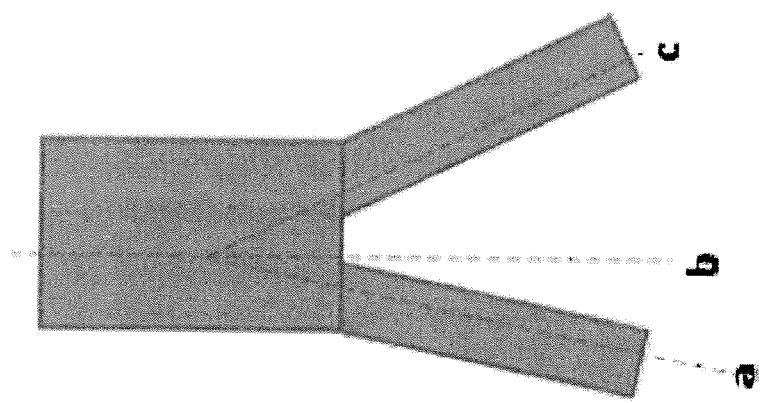
FIG. 17 shows part of a flow cell and axes a, b and c.

The droplet mixture sorting implementation shown in FIG. 16 has parameters:
picodroplet mixture (100 nM AF488 streptavidin in PBS; 10 nM AF488 streptavidin in PBS); injection (160F 120A K chamber 75 um depth single layer device; 2×1375 uL/hr HFE7500; 2500 uL/hr PBS; Droplets: 200 uL/hr); and electric pulse (440 v amplitude; 2.25 ms width; 6-7 ms delay).

The following concerns a picodroplets sorting platform based TR-FRET assay.

Generally, FRET (Fluorescence Resonance Energy Transfer) assays using prompt fluorophores are demonstrated on a microfluidic picodroplet sorting platform. However, the inherited short emission half-lives of prompt fluorophores limits applications involving complex biological fluids or serum, since many compounds and proteins present are naturally fluorescent and thus generate background interference.

Time-resolved FRET (TR-FRET) takes advantage of long-lived emission (300 μs to 2.2 ms) of the fluorescent donors ($Eu^{3+}$ and $Tb^{2+}$ cryptates) upon excitation, such that the lifetime of the acceptor's emission, e.g. d2, is extended. This approach allows the reduction of background fluorescence from complex biological fluids.

An arrangement provides a microfluidic design and optical configuration to enable TR-FRET assays in a microfluidic picodroplet sorting platform. This uses "off-set" detection (using picodroplet movement and a different location) versus electronics, filtering or time-gating and measurement in the same location as the excitation event.

Figure 10:
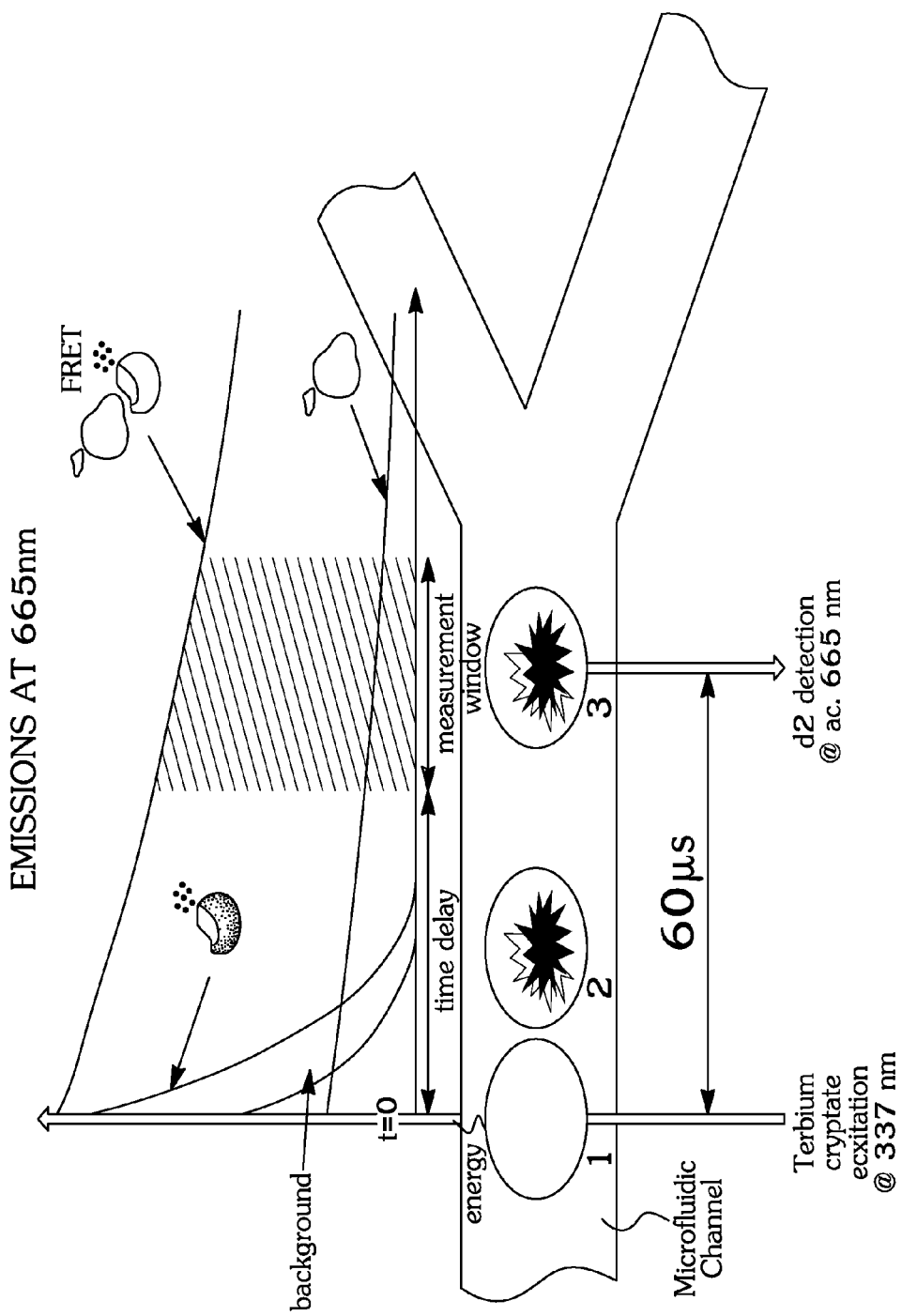
FIG. 10 shows a schematic illustration of TR-FRET assay detection of picodroplets in a microfluidic channel.

TR-FRET assays are generally carried out in a static mode using a conventional microtitre plate (MTP) reader. These are set up to detect an acceptor's fluorescence emission 50-400 μs after excitation of the donor fluorophore. This time delay allows the background fluorescence to rapidly diminish—enabling an improved signal-to-noise ratio with the longer-lived, time-resolved fluorophores. This may be detected with the excitation, emission and detection all being done in a linear or almost linear configuration in the same location. The arrangement however uses picodroplet movement in a defined microfluidic channel to enable excitation of the picodroplet upstream and subsequent detection of emission from that same picodroplet downstream in a different location. The working principle is shown in FIG. 10.

Picodroplet that contains TR-FRET assay reagents are excited at position 1 which corresponds to t=0 in the TR-FRET spectrum. The donor fluorophore, e.g. terbium cryptate, will be excited, e.g. using a 337 nm laser, and emit green light fluorescence. Meanwhile, the acceptor fluorophore, e.g. d2, will be excited as a result of energy transferring in close proximity to the donor fluorophore, and emit red light fluorescence as illustrated in FIG. 1 at position 2. In fact, interfering compounds in complex medium could also emit background fluorescence upon being exposed to the excitation laser reducing specific analyte detection. The background fluorescence normally has a very short half-life time (as illustrated in TR-FRET spectrum of FIG. 1), whereas the donor fluorophore has a much longer half-life that will continuously excite the proximate acceptor fluorophore, e.g. d2, (as illustrated in TR-FRET spectrum of FIG. 1). This allows specific detection of a TR-FRET assay, e.g. at 665 nm wavelength light, in complex medium while reducing fluorescent background by performing detection using a time delay, e.g. 50-400 □s, in a MTP format. This delayed detection can be achieved in picodroplet format in microfluidic channel by monitoring the fluorescent emission at a downstream point along the microfluidic channel, as illustrated at position 3 in FIG. 10 where corresponding to the measurement window in TR-FRET spectrum highlighted as a brown area.

Figure 9:
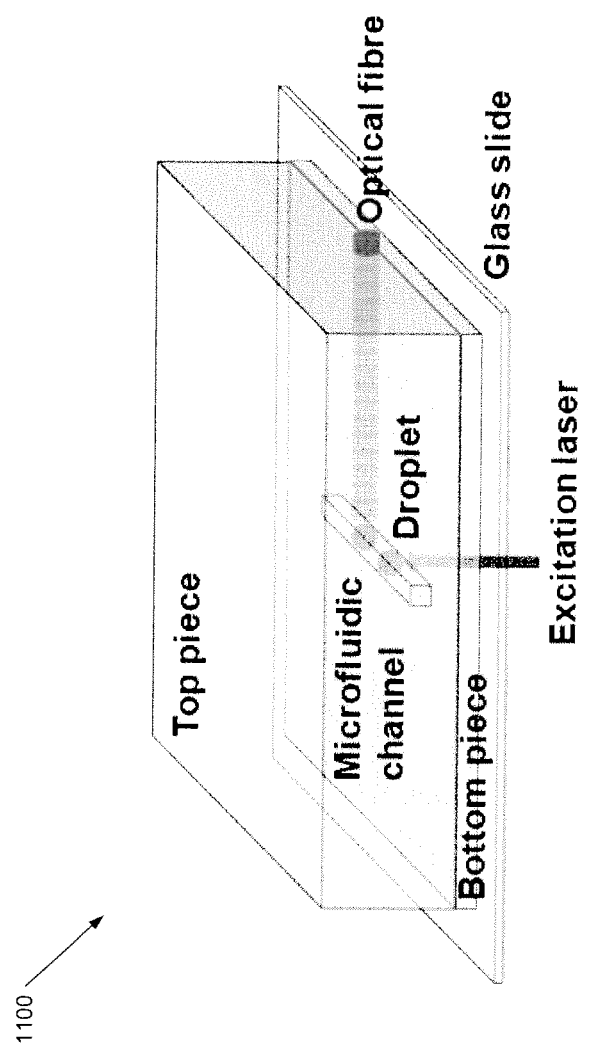
FIG. 9 shows use of an optical fibre, offset from an excitation point, for fluorescence detection, the schematic further illustrating an arrangement of excitation laser beam, microfluidic channel and detection optical fibre.

The downstream detection point along microfluidic channel could be adjusted based on total liquid flow rate in order to sufficiently reduce background fluorescence. An example could be:
1. If the total flow rate is 3600 μL/hr=1 $mm^3$/s;
2. Cross section of channel 50×50 $um^2$=50×$10^{-3}$ × 50 ×$10^{-3}$ $mm^2$=2.5×$10^{-3}$ $mm^2$;
3. Linear speed: 1 $mm^3$/s÷2.5×$10^{-3}$ $mm^2$=400 mm/s;
4. Cis-Bio TR-FRET lag time: 0.05-0.40 ms;
5. Distance between excitation and detection:
5.1. 400 mm/s×0.05×10−3 s=20 μm
5.2. 400 mm/s×0.4×10−3 s=160 μm As fluorescence emission can be detected at any direction, the excitation laser beam and fluorescence monitor could be arranged at different directions and different places. A simplified example of the core part setup is illustrated in FIG. 9.

The excitation laser beam comes from underneath the PDMS device precisely aligning the laser spot within the microfluidic channel. When a picodroplet flows across the laser spot, the donor fluorophores in the picodroplet would be excited, and a FRET event then happens. An optical fibre is aligned in the same level as the microfluidic channel, but at a 90 degree angle to both laser beam and microfluidic channel at a downstream position (20-160 μm) as illustrated in FIG. 9. The 90 degree setup permits the minimum interference of any light source from the laser beam. This also offers significant improvements over MTP based TR-FRET strategies.

Figure 11:
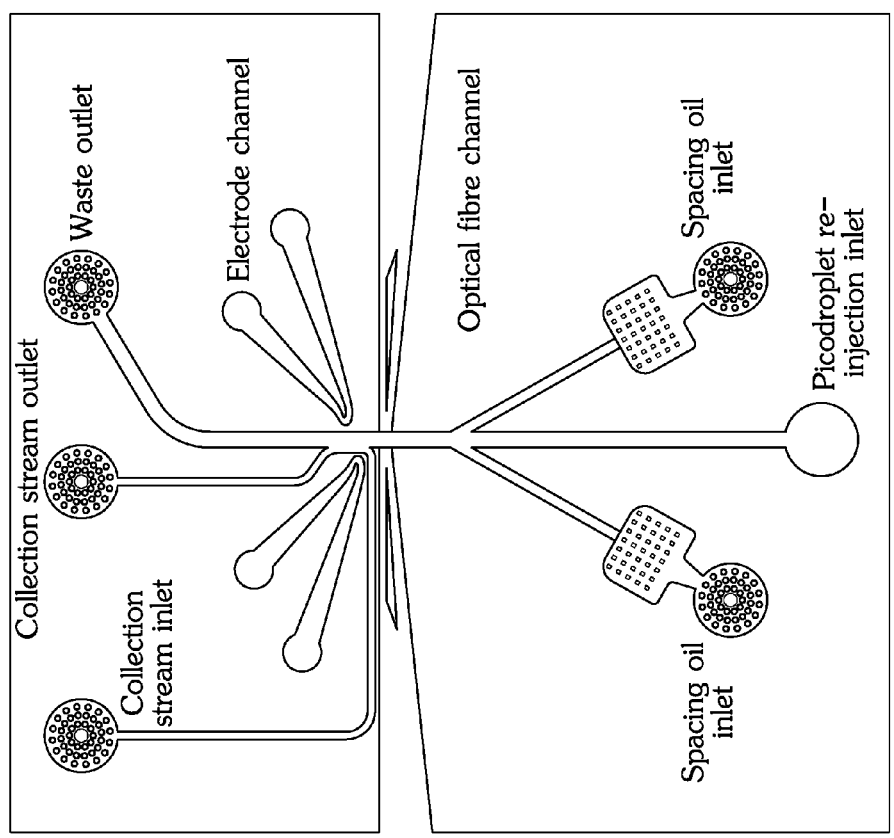
FIG. 11 shows a microfluidic design of integrated picodroplet re-injection unit, optical fibre fluorescence detection unit and fluorescence induced picodroplet selection.

Integrating TR-FRET assay based picodroplet detection with picodroplet re-injection units and fluorescence-induced picodroplet sorting (as illustrated in FIG. 11), may enable scientists to explore a broad range of applications in complex media, e.g. spleen cell screening in serum, hybridoma cell screening in culture media etc., isolation of microorganisms producing unique enzymes.

In view of the above, an arrangement provides a FRET assay in a picodroplet format on a microfluidic platform. Such an arrangement may provide any one or more of the following advantages:
1. Uniquely uses the feature of picodroplet movement along a microfluidic channel and detection at a separate location to deliver the requirement of time lag in TR-FRET assay;
2. The 90 degree setup minimizes the interference of laser source in fluorescence monitoring;
3. Using optical fibres simplify the design and allows miniaturisation of the whole system;
4. This design off-sets the alignment of the excitation and detection optics and electronics.

No doubt many other effective alternatives will occur to the skilled person, such as other time resolved fluorescence assays or luminescence oxygen channeling assays, e.g. It will be understood that the invention is not limited to the described embodiments and encompasses modifications apparent to those skilled in the art lying within the spirit and scope of the claims appended hereto.

The invention claimed is:

1. A flow cell for a microfluidic device for accessing the contents of a droplet of an emulsion in a microfluidic system, the flow cell having:
   a chamber;
   a first microfluidic entry channel and first microfluidic exit channel for flowing said emulsion through said chamber;
   a second microfluidic entry channel and second microfluidic exit channel for flowing a stream of second fluid through said chamber;
   a first electrode having an edge facing a first side of the chamber between the first microfluidic entry channel and the first microfluidic exit channel, said edge substantially straight and substantially parallel to said first side of the chamber; and
   a second electrode having an edge facing a second side of the chamber between the second microfluidic entry channel and the second microfluidic exit channel, said edge substantially straight and substantially parallel to said second side of the chamber,
   wherein, in operation, an interface is formed in said chamber between said emulsion and said stream of second fluid,
   wherein, in operation, said droplet coalesces with said stream of second fluid and said contents of said droplet in said second stream are accessible from said second stream of fluid from said second microtluidic exit channel.

2. A flow cell of claim 1, wherein at least one said edge has length within a range of about 10 micrometers to about 2000 micrometers.

3. A flow cell of claim 1, wherein at least one of said edges is separated from the chamber by a distance within a range of about 1 micrometer to about 200 micrometers.

4. A flow cell of claim 1, wherein a thickness of at least one of said electrodes is within a range of about 1 nanometer to about 500 millimeters.

5. A microfluidic device for detecting a content of a droplet in a stream of fluid, the device comprising;
   a microfluidic channel arranged to conduct said stream of fluid;
   a laser configured to output a laser beam having a wavelength to excite a fluorescent material to output a fluorescence emission;
   a detector having an optical fibre comprising an end facing the microfluidic channel, said end configured to receive said fluorescence emission, the detector arranged to detect a said fluorescence emission propagated through the optical fibre,
   wherein a position of excitation of said fluorescence emission in said microfluidic channel is offset from a part of said microfluidic channel facing the end of the optical fibre; and
   a first electrode facing a first side of the chamber and a second electrode facing a second side of the chamber, said second side opposing said first side,
   the device configured to apply an electric field pulse between said electrodes at a fixed delay after a said fluorescence emission is detected by said detector, if said fluorescence emission exceeds an emission intensity threshold.

6. A microfluidic device of claim 5, configured such that duration of flow of said droplet from position of excitation to said part of said microfluidic channel facing the end of the optical fibre is within a range of about 1 nanosecond to about 1 millisecond.

7. A microfluidic device of claim 5, wherein said end of said optical fibre is separated from the microfluidic channel by a distance of less than about 200 micrometers.

8. A microfluidic device of claim 5, wherein the optical fibre has an optical axis substantially perpendicular to the microfluidic channel.

9. A microfluidic device of claim 5, wherein the laser is arranged to provide said laser beam at substantially 90 degrees to said optical fibre.

10. A microfluidic device of claim 5, wherein said delay is within a range of about 1 microsecond to about 1 second.

11. A microfluidic device of claim 5, configured to apply across said electrodes a voltage to generate said electric field pulse, said voltage within a range of about 10 voltage to about 2000 volts.

12. A method of merging a droplet from an emulsion into a second stream of fluid, the method comprising applying an electric or magnetic field across a flow of said emulsion, the method further comprising controlling a shape of an edge of said field waveform to distort a shape of the droplet such that said droplet when distorted touches said second stream of fluid, the droplet thereby merging with the second stream.

13. The method of claim 12, wherein said controlling said waveform edge shape comprises changing a slew rate of said edge.

14. The method of claim 13, wherein said waveform having said controlled edge shape is a triangular or ramp waveform.

15. The method of claim 13, wherein said controlled edge shape is curved.

16. The method of claim 13, wherein said controlled edge shape comprises a plurality of pulses.

17. A method of detecting a content of a droplet in a stream of fluid, the method comprising exciting and detecting fluorescence emission of a content of the droplet, wherein said content comprises a fluorescent material comprising fluorescent labelled antibody for binding to a cell surface marker, protein, peptide, carbonate, antigen, RNA or DNA dissolved in said content of said droplet and/or cellular probes which detect cell function and viability, the method using a flow cell of claim 1.

18. A method of detecting a content of a droplet in a stream of aqueous fluid carrying at least one said droplet, said at least one said droplet having on average one biological cell per droplet, the method comprising:
   storing a said biological cell in said droplet for substantially 30 minutes or more, wherein said droplet is in said aqueous fluid and said aqueous fluid is a culture medium; and
   using a flow cell of claim, to detect a result of biological activity in said stored cell or a biological molecule or chemical released or secreted from said stored cell.

* * * * *